US008592653B2

(12) United States Patent
Bing et al.

(10) Patent No.: US 8,592,653 B2
(45) Date of Patent: Nov. 26, 2013

(54) CORN EVENT DAS-59122-7 AND METHODS FOR DETECTION THEREOF

(75) Inventors: James Wayne Bing, Ankeny, IA (US); Robert F. Cressman, Jr., Wilmington, DE (US); Manju Gupta, Carmel, IN (US); Salim M. Hakimi, Sacramento, CA (US); David Hondred, Altoona, IA (US); Todd L. Krone, Johnston, IA (US); Mary E. Hartnett Locke, Mickleton, NJ (US); Abigail K. Luckring, West Chester, PA (US); Sandra E. Meyer, Des Moines, IA (US); Daniel Moellenbeck, Granger, IA (US); Kenneth Edwin Narva, Zionsville, IN (US); Paul D. Olson, Kalaheo, HI (US); Craig D. Sanders, Bear, DE (US); Jimei Wang, Johnston, IA (US); Jian Zhang, Urbandale, IA (US); Gan-Yuan Zhong, Urbandale, IA (US)

(73) Assignees: Pioneer Hi-Bred International, Inc., Johnston, IA (US); E.I. du Pont de Nemours and Company, Wilmington, DE (US); Dow Agrosciences LLC, Indianapolis, IN (US)

( * ) Notice: Subject to any disclaimer, the term of this patent is extended or adjusted under 35 U.S.C. 154(b) by 372 days.

(21) Appl. No.: 12/907,488

(22) Filed: Oct. 19, 2010

(65) Prior Publication Data
US 2011/0030086 A1 Feb. 3, 2011

Related U.S. Application Data

(62) Division of application No. 11/938,483, filed on Nov. 12, 2007, which is a division of application No. 11/237,222, filed on Sep. 28, 2005, now Pat. No. 7,323,556.

(60) Provisional application No. 60/614,225, filed on Sep. 29, 2004.

(51) Int. Cl.
*A01H 5/00* (2006.01)
*A01H 5/10* (2006.01)
*A01H 1/00* (2006.01)
*C12Q 1/68* (2006.01)
*C12N 15/32* (2006.01)

(52) U.S. Cl.
USPC ..... 800/302; 800/320.1; 800/260; 536/23.71; 435/6.1

(58) Field of Classification Search
None
See application file for complete search history.

(56) References Cited

U.S. PATENT DOCUMENTS

| 5,474,796 | A | 12/1995 | Brennan |
|---|---|---|---|
| 5,541,308 | A | 7/1996 | Hogan et al. |
| 6,232,063 | B1 | 5/2001 | Beckmann et al. |
| 6,372,480 | B1 | 4/2002 | Narva et al. |
| 6,395,485 | B1 | 5/2002 | De Beuckeleer |
| 6,458,584 | B1 | 10/2002 | Mirzabekov et al. |
| 6,825,400 | B2 | 11/2004 | Behr et al. |
| 7,112,721 | B2 | 9/2006 | Fabijanski et al. |
| 7,323,556 | B2 | 1/2008 | Bing et al. |
| 2002/0013960 | A1 | 1/2002 | Behr et al. |
| 2002/0102582 | A1 | 8/2002 | Levine |
| 2002/0199215 | A1 | 12/2002 | Boets et al. |
| 2003/0198943 | A1 | 10/2003 | Remacle et al. |
| 2006/0141495 | A1 | 6/2006 | Wu |
| 2008/0166725 | A1 | 7/2008 | Bing et al. |
| 2008/0166726 | A1 | 7/2008 | Bing et al. |
| 2008/0171334 | A1 | 7/2008 | Bing et al. |
| 2008/0182256 | A1 | 7/2008 | Bing et al. |

FOREIGN PATENT DOCUMENTS

| EP | 0 857 791 A2 | 12/1998 |
|---|---|---|
| EP | 1 167 531 A1 | 2/2002 |
| WO | WO 84/02913 | 8/1984 |
| WO | WO 01/14417 | 3/2001 |
| WO | WO 02/15701 | 2/2002 |
| WO | WO 03/052073 | 6/2003 |
| WO | WO 2004/011601 A2 | 2/2004 |
| WO | WO 2004/011702 A2 | 2/2004 |

OTHER PUBLICATIONS

Whitelaw et al (2003, GenBank Accession No. CG069192).*
Buck, et al., "Design Strategies and Performance of Custom DNA Sequencing Primers," *BioTechniques*, 1999, vol. 27, pp. 528-536.
Crickmore, et al., http://www.lifesci.sussex.ac.uk/Home/Neil_Crickmore/Bt/, 2009, pp. 1-11.
Herman, et al., "Binary Insecticidal Crystal Protein from *Bacillus thuringiensis*, Strain PS149B1: Effects of Individual Protein Components and Mixtures in Laboratory Bioassays," *Journal of Economic Entomology*, 2002, vol. 95(3), pp. 635-639.
Hunst and Rood, Application for the Determination of Nonregulated Status for B*t* Cry/34/35Ab1 Insect-Resistant, Glufosinate-Tolerant Corn: Corn Line 59122, U.S. Department of Agriculture, Animal and Plant Health Inspection Service, 2004, pp. 1-237, XP 002384226.
Lowe, et al., "A computer program for selection of oligonucleotide primers for polymerase chain reactions," *Nucleic Acids Research*, 1990, vol. 18(7), pp. 1757-1761.
Moellenbeck, et al., "Insecticidal proteins from *Bacillus thuringiensis* protect corn from corn rootworms," *nature biotechnology*, 2001, vol. 19, pp. 668-672.
Ricker, Karin, Biotechnology Consultation Note to the File BNF No. 000081, U.S. Food and Drug Administration (2004), pp. 1-6, XP002384225.
Stratagene Catalog, p. 40, 1988.

(Continued)

*Primary Examiner* — Anne Kubelik
(74) *Attorney, Agent, or Firm* — Ballard Spahr LLP

(57) ABSTRACT

The invention provides DNA compositions that relate to transgenic insect resistant maize plants. Also provided are assays for detecting the presence of the maize DAS-59122-7 event based on the DNA sequence of the recombinant construct inserted into the maize genome and the DNA sequences flanking the insertion site. Kits and conditions useful in conducting the assays are provided.

8 Claims, 7 Drawing Sheets

(56) References Cited

OTHER PUBLICATIONS

Sequence Search Reports, OM nucleic—nucleic search, 2009, pp. 1-6.
Whitelaw, et al. PUFTW67TB ZM_0.6_1.0KB *Zea mays* genomic clone ZMMBTa0732K13, genomic survey sequence, 2003, EMBL Accession No. CG069192.
Whitelaw, et al. GenBank Accession No. BZ739496, 2003.
Zambryski, et al., GenBank Accession N. TIP37TD2, 1996.
Hammack, L., et al., "Larval Sampling and Instar Determination in Field Populations of Northern and Western Corn Rootworm (Coleoptera: Chrysomelidae)," Journal of Economic Entomology, 2003, vol. 96(4), pp. 1153-1159.
Ellis, et al., "Novel *Bacillus thuringiensis* Binary Insecticidal Crystal Proteins Active on Western corn Rootworm, *Diabrotica virgifera virgifera* LeConte," App and Envir Microbiology, 2002, vol. 68(3), pp. 1137-1145, XP002985898.

* cited by examiner

FIG. 1

```
   1  CTGAGCGCAC AACAGCGAGT CGCATGGCAC CGGACGACAT GAGCGAGATT
  51  TAGATCGGAG GGTGCGGACA TGGGGCAACC TGCGCAGCTA ACGCAGGGAT
 101  CCACACGACC ACCAACGAAG CCAAGCCCGG GCACGTCCCC AGGCAGGTTG
 151  GGCCCTGGTT CCACCAGCGG ATGCATGCAG TGAAGCGGGG ACGGAGAGAC
 201  AAGCCGAGGG CGCGGGTGGG AATGGCGTCC GGGAGGACGA GTGGAGGAGA
 251  AGAATCTAGA GGCATCGAGA TTCGAGAAGC CGACGGAGAC AAGATTCGTG
 301  TGGGGGGAGA CAAACCGCGG GGCTGAGCGC CGTTGATATG GGATCAGACG
 351  GTGTGGATAA AAAAAGTGAC GTTGATAGAA CGTCTGGCCA GTGAAAAAAC
 401  AAAACAACTC CAACAAAATA CTTTAAAAGC TCTTATACCC TAAATGTAGG
 451  GGATCAAACA CGTCTCTACA CTATTTAGCA GCGTCCTCTA AATGATCCTC
 501  TAAATTTAGA GAACGCTACT AGATTCTCTA TATATAGTTT CTCTAAACGA
 551  TCTTTTATCC ATTTAAATAC TTTAAATAAC CGGTTTAACA AAACTAAAAT
 601  ATATACAATA CATTTGAGAG TATGACAAAT ACGTATGTAT AAAAATAAAA
 651  AATAAAAATAA TGTATTAGTC TACTTTGAAT CTTCTTTTCT TCATAATATA
 701  ATGATGTATA GCTCTCATGT GCGTTGAGAA AAAAGTTAGA GCTAGACGTT
 751  TAATGTGTAG TGACAGTCTT CGACGAAATC TCCCTAATGA GATGAATTAC
 801  TGGAGGTTCC ATCAGAAAGT CCCCTGAAAA GAGGCATTTA TTTAGTTTAG
 851  TCAGCAATTT CTGGGAACAC AAATATTCTT TTGTTATCAC CACTATTAAA
 901  AATCTATGGT TATAACTTAT AATAACATGA AAAAATAATT TAGCATCCCA
 951  TATATATAAA AACTGAAGGA AGCCATATAT ACTAACATAA GTTAGGAGAA
1001  ACTAAGAAGG TTGTGCAAAG CTTGCACTGC TCCAAAATAC TGCAAACAAC
1051  CACTCTCCTC TACCAACCAA AGAAACTCAT GTACTCCCTC CGTTCTTTTT
1101  TATTTGTCGC ATTTTAGTTT AAAAATGAAC TAGCAGTCGA CAAATATTCG
1151  AGAACAGATA TAGTATATAC TAACATAACT TAGGAGATAC TAAGAAAGTT
1201  GCGCAGAGCT TTCACTGTTC CAAATTACTG CAAAGCCTCT CCCCTCTGCC
1251  AGTACATCTA CGAGATGTTT CAGTTAAACA AAGATTCAGA CAAGTGATGA
1301  GCCACTTCTT GTCATAGATT GTGTGGTCAA CCAACCCATT GATGCCACGG
1351  TTTTTGTGCA TCCATGCTTT TGTATTAAAA CATCAGTTAT GTTTACCATG
1401  TCCGATATGC TCTACATAAT GACAATCAAC TTGGTGTTCA TTATATTTAC
1451  AATGTTAGGA ATTTCAATAG CTACGAACAC TTCAATAGAA GTGCCTTTGT
1501  GGGATCACCT TAATGTGTTG TTGATGTAAG GAGAAGAATC TTAATTTACT
1551  CTTGCTAAAT TTGAACTACA CAAAACCACT GCACTGAGGA TTGTCCTAAT
1601  AAATTACTGC TCATACACGT TAGCATCTGT TCAGATACTG AGCTAATCCC
1651  TAGGATTAAA GGATTTGTAA AAGATATGCC CAATCATTCA TTTTAGTTAT
1701  TTATTTCTTA GTTATCCACT TGAAGATTTA CATACATTTG AAATAAATTT
1751  CTTAGAGGTA AAGTGAAAAT CAGTTATTTA AATACATTTT AGTTATTTAT
1801  TTTCTTCTTT TTCCTAATTT TTCCTTGTAT TTGAAGTCTG AAAAGATAAC
1851  TTTGCCCTTA TACATATTTT ATCTTCTACG TACGCATCTG AACAACGTCT
1901  CTTTGTCCCC TGATCGTGCA GCAATTAGTG CTATGAATCG CGTTTAAGCG
1951  CTGCAAAATC ATGGCTGGGG CTTCGTCCTC GAGTCGTCCT GCTGCTCGAT
2001  GTCACCTCGA GTCCCGCACC GACCTCAGTG CTTGTTCTTG TTGGAGCCAC
2051  CTCTCTCGGA CGATCGCCAA AGACGGATAA GGCCGAAGCC GTCACTTCAG
2101  ACCGCGCTCA TGCGCCGTAG CAGACTCCTA CATAGCAGGG CCAGGGTATG
2151  TGGACCTTTG CAAGTTTAGG ATTGGAACCA GCGACCAGAA TCCACAAGAT
2201  TGGAGCAAAC GACCAAAAAT TCACAAGGAT TGGCGGCTGA CATTGCCAGC
2251  GCGGGATCGC ATGCGGCGGC GGCGGCCGGG GCGAGCACGG GAGCAGGCGA
2301  CAGTCGAGCT CCATTGGAAC GTAGAAATAC TTAAGGGCAA GGTCTCCAAA
2351  TACTTGAAAA AATAGGAAAA AGAAGAAAAT ACATGAAATG ATATTGAAAT
2401  CAATTGGAAG ATGTTATGAA TCTTGTTTTT GCAAAGCGAA CGATTCAGAT
2451  GGCAAAACTA TGAATCTTTT TGTTTGAAGT CCCAAATATA AAATTTTCTC
2501  GTACTCACCA ACATTGGTGC GCACCTGTGA TTGGCTCATA AAAATTCTTG
2551  GAGGGACGGA AGAAAGAGTG AAGGGATAAG CAAGTAAAAG CGCTCAAACA
2601  CTGATAGTTT AAACTGAAGG CGGGAAACGA CAATCTGATC ATGAGCGGAG
```

FIG. 1 continued

```
2651  AATTAAGGGA  GTCACGTTAT  GACCCCCGCC  GATGACGCGG  GACAAGCCGT
2701  TTTACGTTTG  GAACTGACAG  AACCGCAACG  TTGAAGGAGC  CACTCAGCAA
2751  GCTTACTAGT  AGCGCTGTTT  AAACGCTCTT  CAACTGGAAG  AGCGGTTACC
2801  CGGACCGAAG  CTTGCATGCC  TGCAGTGCAG  CGTGACCCGG  TCGTGCCCCT
2851  CTCTAGAGAT  AATGAGCATT  GCATGTCTAA  GTTATAAAAA  ATTACCACAT
2901  ATTTTTTTTG  TCACACTTGT  TTGAAGTGCA  GTTTATCTAT  CTTTATACAT
2951  ATATTTAAAC  TTTACTCTAC  GAATAATATA  ATCTATAGTA  CTACAATAAT
3001  ATCAGTGTTT  TAGAGAATCA  TATAAATGAA  CAGTTAGACA  TGGTCTAAAG
3051  GACAATTGAG  TATTTTGACA  ACAGGACTCT  ACAGTTTTAT  CTTTTTAGTG
3101  TGCATGTGTT  CTCCTTTTTT  TTTGCAAATA  GCTTCACCTA  TATAATACTT
3151  CATCCATTTT  ATTAGTACAT  CCATTTAGGG  TTTAGGGTTA  ATGGTTTTTA
3201  TAGACTAATT  TTTTTAGTAC  ATCTATTTTA  TTCTATTTTA  GCCTCTAAAT
3251  TAAGAAAACT  AAAACTCTAT  TTTAGTTTTT  TTATTTAATA  ATTTAGATAT
3301  AAAATAGAAT  AAAATAAAGT  GACTAAAAAT  TAAACAAATA  CCCTTTAAGA
3351  AATTAAAAAA  ACTAAGGAAA  CATTTTTCTT  GTTCGAGTA  GATAATGCCA
3401  GCCTGTTAAA  CGCCGTCGAC  GAGTCTAACG  GACACCAACC  AGCGAACCAG
3451  CAGCGTCGCG  TCGGGCCAAG  CGAAGCAGAC  GGCACGGCAT  CTCTGTCGCT
3501  GCCTCTGGAC  CCCTCTCGAG  AGTTCCGCTC  CACCGTTGGA  CTTGCTCCGC
3551  TGTCGGCATC  CAGAAATTGC  GTGGCGGAGC  GGCAGACGTG  AGCCGGCACG
3601  GCAGGCGGCC  TCCTCCTCCT  CTCACGGCAC  CGGCAGCTAC  GGGGGATTCC
3651  TTTCCCACCG  CTCCTTCGCT  TTCCCTTCCT  CGCCCGCCGT  AATAAATAGA
3701  CACCCCCTCC  ACACCCTCTT  TCCCCAACCT  CGTGTTGTTC  GGAGCGCACA
3751  CACACACAAC  CAGATCTCCC  CCAAATCCAC  CCGTCGGCAC  CTCCGCTTCA
3801  AGGTACGCCG  CTCGTCCTCC  CCCCCCCCCC  CTCTCTACCT  TCTCTAGATC
3851  GGCGTTCCGG  TCCATGGTTA  GGGCCCGGTA  GTTCTACTTC  TGTTCATGTT
3901  TGTGTTAGAT  CCGTGTTTGT  GTTAGATCCG  TGCTGCTAGC  GTTCGTACAC
3951  GGATGCGACC  TGTACGTCAG  ACACGTTCTG  ATTGCTAACT  TGCCAGTGTT
4001  TCTCTTTGGG  GAATCCTGGG  ATGGCTCTAG  CCGTTCCGCA  GACGGGATCG
4051  ATTTCATGAT  TTTTTTTGTT  TCGTTGCATA  GGGTTTGGTT  TGCCCTTTTC
4101  CTTTATTTCA  ATATATGCCG  TGCACTTGTT  TGTCGGGTCA  TCTTTTCATG
4151  CTTTTTTTTG  TCTTGGTTGT  GATGATGTGG  TCTGGTTGGG  CGGTCGTTCT
4201  AGATCGGAGT  AGAATTCTGT  TTCAAACTAC  CTGGTGGATT  TATTAATTTT
4251  GGATCTGTAT  GTGTGTGCCA  TACATATTCA  TAGTTACGAA  TTGAAGATGA
4301  TGGATGGAAA  TATCGATCTA  GGATAGGTAT  ACATGTTGAT  GCGGGTTTTA
4351  CTGATGCATA  TACAGAGATG  CTTTTTGTTC  GCTTGGTTGT  GATGATGTGG
4401  TGTGGTTGGG  CGGTCGTTCA  TTCGTTCTAG  ATCGGAGTAG  AATACTGTTT
4451  CAAACTACCT  GGTGTATTTA  TTAATTTTGG  AACTGTATGT  GTGTGTCATA
4501  CATCTTCATA  GTTACGAGTT  TAAGATGGAT  GGAAATATCG  ATGTAGGATA
4551  GGTATACATG  TTGATGTGGG  TTTTACTGAT  GCATATACAT  GATGGCATAT
4601  GCAGCATCTA  TTCATATGCT  CTAACCTTGA  GTACCTATCT  ATTATAATAA
4651  ACAAGTATGT  TTTATAATTA  TTTTGATCTT  GATATACTTG  GATGATGGCA
4701  TATGCAGCAG  CTATATGTGG  ATTTTTTTAG  CCCTGCCTTC  ATACGCTATT
4751  TATTTGCTTG  GTACTGTTTC  TTTTGTCGAT  GCTCACCCTG  TTGTTTGGTG
4801  TTACTTCTGC  AGGTCGACTC  TAGAGGATCC  ACACGACACC  ATGTCCGCCC
4851  GCGAGGTGCA  CATCGACGTG  AACAACAAGA  CCGGCCACAC  CCTCCAGCTG
4901  GAGGACAAGA  CCAAGCTCGA  CGGCGGCAGG  TGGCGCACCT  CCCCGACCAA
4951  CGTGGCCAAC  GACCAGATCA  AGACCTTCGT  GGCCGAATCC  AACGGCTTCA
5001  TGACCGGCAC  CGAGGGCACC  ATCTACTACT  CAATTAATGG  CGAGGCCGAG
5051  ATCAGCCTCT  ACTTCGACAA  CCCGTTCGCC  GGCTCCAACA  AATACGACGG
5101  CCACTCCAAC  AAGTCCCAGT  ACGAGATCAT  CACCCAGGGC  GGCTCCGGCA
5151  ACCAGTCCCA  CGTGACCTAC  ACCATCCAGA  CCACCTCCTC  CCGCTACGGC
5201  CACAAGTCCT  GAGTCATGAG  TCATGAGTCA  GTTAACCTAG  ACTTGTCCAT
5251  CTTCTGGATT  GGCCAACTTA  ATTAATGTAT  GAAATAAAAG  GATGCACACA
```

FIG. 1 continued

```
5301    TAGTGACATG CTAATCACTA TAATGTGGGC ATCAAAGTTG TGTGTTATGT
5351    GTAATTACTA GTTATCTGAA TAAAAGAGAA AGAGATCATC CATATTTCTT
5401    ATCCTAAATG AATGTCACGT GTCTTTATAA TTCTTTGATG AACCAGATGC
5451    ATTTCATTAA CCAAATCCAT ATACATATAA ATATTAATCA TATATAATTA
5501    ATATCAATTG GGTTAGCAAA ACAAATCTAG TCTAGGTGTG TTTTGCGAAT
5551    GCGGCCGCGG ACCGAATTGG GGATCTGCAT GAAAGAAACT GTCGCACTGC
5601    TGAACCGCAC CTTGTCACTT TCATCGAACA CGACCTGTGC CCAAGATGAC
5651    GGTGCTGCGG TCTAAGTGAG CTGAATTGC CTTGGACAGA AGCGGACTCC
5701    CTACAATTAG TTAGGCCAAA CGGTGCATCC ATGTGTAGCT CCGGGCTCGG
5751    GCTGTATCGC CATCTGCAAT AGCATCCATG GAGCTCGTTC CATGTAGTTG
5801    GAGATGAACC AATGATCGGG CGTGTGGACG TATGTTCCTG TGTACTCCGA
5851    TAGTAGAGTA CGTGTTAGCT CTTTCATGGT GCAAGTGAAA TTTGTGTTGG
5901    TTTAATTACC CCTACGTTAG TTGCGGGACA GGAGACACAT CATGAATTTA
5951    AAGGCGATGA TGTCCTCTCC TGTAATGTTA TTCTTTTGAT GTGATGAATC
6001    AAAATGTCAT ATAAAACATT TGTTGCTCTT TAGTTAGGCC TGATCGTAGA
6051    ACGAAATGCT CGTGTAGCGG GGCTACGAGC CTATGACGCA ATAACACTGG
6101    TTTGCCGGCC CGGAGTCGCT TGACAAAAAA AAGCATGTTA AGTTTATTTA
6151    CAATTCAAAA CCTAACATAT TATATTCCCT CAAAGCAGGT TCACGATCAC
6201    ACCTGTACCT AAAAAAAACA TGAAGAATAT ATTACTCCAT TATTATGAGA
6251    TGAACCACTT GGCAAGAGTG GTAAGCTATA TAAAAAAATG AACATTATTA
6301    CGAGATGTTA TATGCCATTA TATTGATTCG AAGATATATG TTTCTTTCTC
6351    CCACGGGCAC CTAACGGATA CATGATAAGG CCAAGGCAGA TCACGGGAAA
6401    TTATTCGAAT ACATGTTACG CCCTATTGCC GGAAAAAAAA TGCAGGGCAG
6451    GTGTTGGCCG TAGCGATTTA AGCACTTAAG CTGGAGGTTG CCACACTTGG
6501    ATGCAAGCGT CTGACCCTTC TAAAACATCG GCGGCTTTGT CCGTATCCGT
6551    ATCCCCTATC CGACATCTAG CTGGCCACAC GACGGGCTG GGCAGATCGT
6601    GGATGCCGGG TCGACGTCGA TCGTCAGCCA TCATAGACCA ATCGACCATC
6651    TGTTATGGAT GCTTGCTAGC TAGACTAGTC AGACATAAAA TTTGGATACT
6701    TTCTCCCAAC TGGGAGACGG GGACTGATGT GCAGCTGCAC GTGAGCTAAA
6751    TTTTTCCCTA TAAATATGCA TGAAATACTG CATTATCTTG CCACAGCCAC
6801    TGCCACAGCC AGATAACAAG TGCAGCTGGT AGCACGCAAC GCATAGCTCT
6851    GGACTTGTAG CTAGGTAGCC AACCGGATCC ACACGACACC ATGCTCGACA
6901    CCAACAAGGT GTACGAGATC AGCAACCACG CCAACGGCCT CTACGCCGCC
6951    ACCTACCTCT CCCTCGACGA CTCCGGCGTG TCCCTCATGA ACAAGAACGA
7001    CGACGACATC GACGACTACA ACCTCAAGTG GTTCCTCTTC CCGATCGACG
7051    ACGACCAGTA CATCATCACC TCCTACGCCG CCAACAACTG CAAGGTGTGG
7101    AACGTGAACA ACGACAAGAT TAATGTGTCA ACCTACTCCT CCACCAACTC
7151    CATCCAGAAG TGGCAGATCA AGGCCAACGG CTCCTCCTAC GTGATCCAGT
7201    CCGACAACGG CAAGGTGCTC ACCGTCGGCA CCGGCCAGGC CCTCGGCCTC
7251    ATCCGCCTCA CCGACGAGTC CTCCAACAAC CCGAACCAGC AATGGAACCT
7301    GACGTCCGTG CAGACCATCC AGCTCCCGCA GAAGCCGATC ATCGACACCA
7351    AGCTCAAGGA CTACCCGAAG TACTCCCCGA CCGGCAACAT CGACAACGGC
7401    ACCTCCCCGC AGCTCATGGG CTGGACCCTC GTGCCGTGCA TCATGGTGAA
7451    CGACCCGAAC ATCGACAAGA ACACCCAGAT CAAGACCACC CCGTACTACA
7501    TCCTCAAGAA GTACCAGTAC TGGCAGAGGG CCGTGGGCTC CAACGTCGCG
7551    CTCCGCCCGC ACGAGAAGAA GTCCTACACC TACGAGTGGG GCACCGAGAT
7601    CGACCAGAAG ACCACCATCA TCAACACCCT CGGCTTCCAG ATCAACATCG
7651    ACAGCGGCAT GAAGTTCGAC ATCCCGGAGG TGGGCGGCAG TACCGACGAG
7701    ATCAAGACCC AGCTCAACGA GGAGTCAAG ATCGAGTATT CACATGAGAC
7751    GAAGATCATG GAGAAGTACC AGGAGCAGTC CGAGATCGAC AACCCGACCG
7801    ACCAGTCCAT GAACTCCATC GGCTTCCTCA CCATCACCTC CCTGGAGCTC
7851    TACCGCTACA ACGGCTCCGA GATCCGCATC ATGCAGATCC AGACCTCCGA
7901    CAACGACACC TACAACGTGA CCTCCTACCC GAACCACCAG CAGGCCCTGC
```

FIG. 1 continued

```
 7951    TGCTGCTGAC  CAACCACTCC  TACGAGGAGG  TGGAGGAGAT  CACCAACATC
 8001    CCGAAGTCCA  CCCTCAAGAA  GCTCAAGAAG  TACTACTTCT  GAGTCATGAG
 8051    TCATGAGTCA  GTTAACCTAG  ACTTGTCCAT  CTTCTGGATT  GGCCAACTTA
 8101    ATTAATGTAT  GAAATAAAAG  GATGCACACA  TAGTGACATG  CTAATCACTA
 8151    TAATGTGGGC  ATCAAAGTTG  TGTGTTATGT  GTAATTACTA  GTTATCTGAA
 8201    TAAAGAGAA   AGAGATCATC  CATATTTCTT  ATCCTAAATG  AATGTCACGT
 8251    GTCTTTATAA  TTCTTTGATG  AACCAGATGC  ATTTCATTAA  CCAAATCCAT
 8301    ATACATATAA  ATATTAATCA  TATATAATTA  ATATCAATTG  GGTTAGCAAA
 8351    ACAAATCTAG  TCTAGGTGTG  TTTTGCGAAT  TCCCATGGAG  TCAAAGATTC
 8401    AAATAGAGGA  CCTAACAGAA  CTCGCCGTAA  AGACTGGCGA  ACAGTTCATA
 8451    CAGAGTCTCT  TACGACTCAA  TGACAAGAAG  AAAATCTTCG  TCAACATGGT
 8501    GGAGCACGAC  ACGCTTGTCT  ACTCCAAAAA  TATCAAAGAT  ACAGTCTCAG
 8551    AAGACCAAAG  GGCAATTGAG  ACTTTTCAAC  AAAGGGTAAT  ATCCGGAAAC
 8601    CTCCTCGGAT  TCCATTGCCC  AGCTATCTGT  CACTTTATTG  TGAAGATAGT
 8651    GGAAAAGGAA  GGTGGCTCCT  ACAAATGCCA  TCATTGCGAT  AAAGGAAAGG
 8701    CCATCGTTGA  AGATGCCTCT  GCCGACAGTG  GTCCAAAGA   TGGACCCCCA
 8751    CCCACGAGGA  GCATCGTGGA  AAAAGAAGAC  GTTCCAACCA  CGTCTTCAAA
 8801    GCAAGTGGAT  TGATGTGATA  TCTCCACTGA  CGTAAGGGAT  GACGCACAAT
 8851    CCCACTATCC  TTCGCAAGAC  CCTTCCTCTA  TATAAGGAAG  TTCATTTCAT
 8901    TTGGAGAGGA  CAGGGTACCC  GGGGATCCAC  CATGTCTCCG  GAGAGGAGAC
 8951    CAGTTGAGAT  TAGGCCAGCT  ACAGCAGCTG  ATATGGCCGC  GGTTTGTGAT
 9001    ATCGTTAACC  ATTACATTGA  GACGTCTACA  GTGAACTTTA  GGACAGAGCC
 9051    ACAAACACCA  CAAGAGTGGA  TTGATGATCT  AGAGAGGTTG  CAAGATAGAT
 9101    ACCCTTGGTT  GGTTGCTGAG  GTTGAGGGTG  TTGTGGCTGG  TATTGCTTAC
 9151    GCTGGGCCCT  GGAAGGCTAG  GAACGCTTAC  GATTGGACAG  TTGAGAGTAC
 9201    TGTTTACGTG  TCACATAGGC  ATCAAAGGTT  GGGCCTAGGA  TCCACATTGT
 9251    ACACACATTT  GCTTAAGTCT  ATGGAGGCGC  AAGGTTTTAA  GTCTGTGGTT
 9301    GCTGTTATAG  GCCTTCCAAA  CGATCCATCT  GTTAGGTTGC  ATGAGGCTTT
 9351    GGGATACACA  GCCCGGGGTA  CATTGCGCGC  AGCTGGATAC  AAGCATGGTG
 9401    GATGGCATGA  TGTTGGTTTT  TGGCAAAGGG  ATTTGAGTT   GCCAGCTCCT
 9451    CCAAGGCCAG  TTAGGCCAGT  TACCCAGATC  TGAGTCGACC  TGCAGGCATG
 9501    CCCGCTGAAA  TCACCAGTCT  CTCTCTACAA  ATCTATCTCT  CTCTATAATA
 9551    ATGTGTGAGT  AGTTCCCAGA  TAAGGGAATT  AGGGTTCTTA  TAGGGTTTCG
 9601    CTCATGTGTT  GAGCATATAA  GAAACCCTTA  GTATGTATTT  GTATTTGTAA
 9651    AATACTTCTA  TCAATAAAAT  TTCTAATTCC  TAAAACCAAA  ATCCAGGGCG
 9701    AGCTCGGTAC  CCGGGGATCC  TCTAGAGTCG  ACCTGCAGGC  ATGCCCGCGG
 9751    ATATCGATGG  GCCCCGGCCG  AAGCTTCGGT  CCGGGCCATC  GTGGCCTCTT
 9801    GCTCTTCAGG  ATGAAGAGCT  ATGTTTAAAC  GTGCAAGCGC  TCAATTCGCC
 9851    CTATAGTGAG  TCGTATTACA  ATCGTACGCA  ATTCAGTACA  TTAAAAACGT
 9901    CCGCAATGTG  TTATTAAGTT  GTCTAAGCGT  CAATTTTTCC  CTTCTATGGT
 9951    CCCGTTTGTT  TATCCTCTAA  ATTATATAAT  CCAGCTTAAA  TAAGTTAAGA
10001    GACAAACAAA  CAACACAGAT  TATTAAATAG  ATTATGTAAT  CTAGATACCT
10051    AGATTATGTA  ATCCATAAGT  AGAATATCAG  GTGCTTATAT  AATCTATGAG
10101    CTCGATTATA  TAATCTTAAA  AGAAACAAA   CAGAGCCCCT  ATAAAAAGGG
10151    GTCAAGTGGA  CACTTGGTCA  CTCATTTAAT  CCCTCCCTCT  CCTCTTTTAT
10201    CCCTCTTTTT  GGTGTATTCA  CCAATAGTGG  TGTGCACCTG  TGATTGGCTC
10251    GTAAAAATTC  TTGGACGGAT  GGAAGAGTGA  AGAGATAAGC  AAGTCAAAGA
10301    AAAGTAACAA  CGAAGCTTCA  TCAGCTACAA  ATTTTGGCCC  AACTGGTTGC
10351    ACCAGCACCA  AACTTACGTA  TACATGATTA  TCTCTGTTTC  CCTCATTTCG
10401    AAGAAAAAAA  CGGGTTTCAA  AACCCACTGC  TTTCAGGAGT  AAAAAAAGAT
10451    AATAATCTGA  AACATTGCTT  CCACCTTGGC  CCTTATTGG   TTACGTTGCA
10501    ATTCACCCCA  ATCCACATGT  GGATTGAGAT  GGATTGCAGT  GTAGCTAGAC
10551    AAACCCTTAG  GCCCTGTTTG  CATAGGAATA  CACCAGGAAT  TATTCCAGCT
```

FIG. 1 continued

```
10601  AATCAAAATT TATATAAATG AGAGAAACAA TTCGGATAGG AATTGTTCCA
10651  GGACTTCATT CTGCAGTAAC CGAACGGCCC CTTAATCCAC CCCAATACAC
10701  GTGGATTGGA GTGGATTGAG GTACAGCCAA ACAAGGCCTA AGTGCAGATC
10751  AAATAAATCA CCCGTCATAT TCTTCTACCT ACAAAAACAG CAATAAACAC
10801  CTGAATGAAG TTCTAATTTG CACAGTGTAG GTAGGATGAA AATAGTTACC
10851  TCCTCATGGT CAGTAACTCT TGGCACACAA CTTCACATGT AATCGATGTA
10901  CCACTTGGCT CTTGCCTGAA ACCCAATACA TCTTTAGCAT AAGAATAATA
10951  TTATGATGGC AAGGCATGAT CACCAGCACT CCTTTATTGT TTAGTAAGTC
11001  TATCACTCCC CAAAACAATT CAAATGAACA GAGATGCATT GCCCCCAATG
11051  AATTCTATTT CAATTAGCCG GAAAATTCTA CTTCATCAGA AGCATCCAAA
11101  TTGCCAGCAT CCCTACTAGA CTGACCATGA CCAGGCTGCC GCAGATGCCT
11151  CTTTTTCTGT CCTCTCCTCT TTGCCTTGAG TTTCTCTTCA AGATCCCTCA
11201  CCCCACGTCT CTTATACATC TTAAAGCTAA CATGTCTCTC CTCCGCCATC
11251  TTCCTAACCT TCTCAGTAAT CTCAGCAGCA ATCTGACGGT TGTACAACTT
11301  CTTCAGCCCC TTCATCAACT TTGCAAATGT GTCAGGCTGT GGCATCAGTC
11351  CTGCCTCTAG CATGTCTAAG CAATACAGGC AGGCCTCCTT GACATGTTTC
11401  TTCGCAAACA GTGCATGAAT CCAGATAGTC CATGCACTCA CATTGAGCTC
11451  ACAGCCTTTG CTCACAATAC ATTTCCAAAC ATCCTTTGCA AGCTCAAGTT
11501  TCTCATCTCT GACCAACGCA TTGAGGAGGT CCTTCAGCAC CCCATATTGC
11551  GGTACCACAA AGAGCCCCCT CCCAACCATG TCTTTAAAAT AACTACATGC
11601  CTCAATCAGC AAACCCTGCC CAACAAGGCC ACTCACCACG ATAGCAAATG
11651  TATCGACCAC AGGACTGAGC CCAGCACTTT CCATCTCATT CCACCAATGTC
11701  ATGGCTTGCT TGGTCTCCCC AAGCCTGCAG GCCAACCGAA TCACCACATT
11751  GTATATCTTG AGATCTGGTG GACACCGGCA CTCCCGCATC CTCTCCATCA
11801  GCTCCAAGCA CTCCTCAAGC TGCTCCTTCT TCTCGTGTGC TACAAAGAAA
11851  CCATGGTACA CGGCAGCGTC CACCCGCAGG CCATCCCTCG ACATAGCATC
11901  CAAGAACTCG TACCCCTGGG AT
```

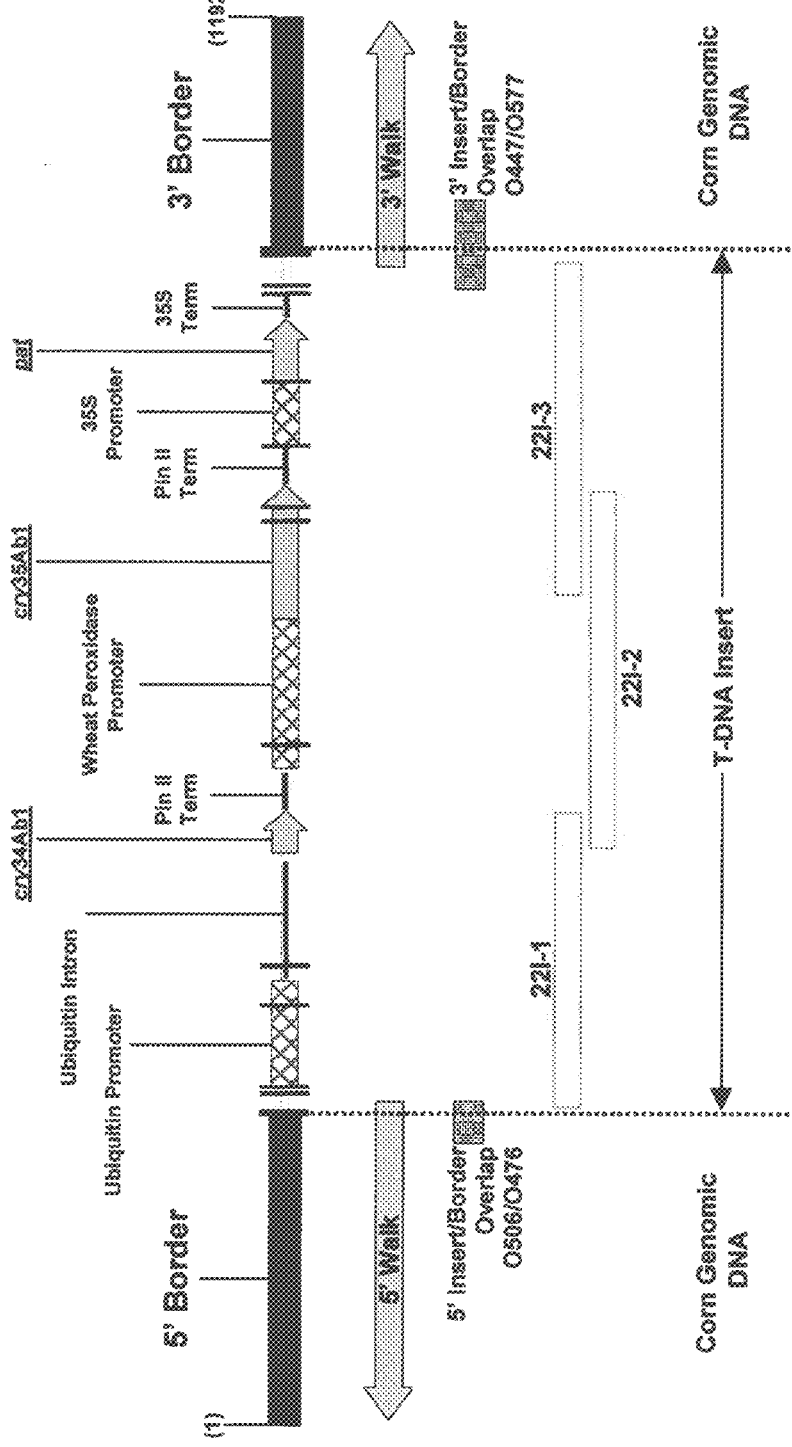

SEQUENCE LISTING

<160> NUMBER OF SEQ ID NOS: 40

<210> SEQ ID NO 1
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 1
gtggctcctt caacgttgcg gttctgtc                              28

<210> SEQ ID NO 2
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 2
cgtgcaagcg ctcaattcgc cctatagtg                             29

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 3
aattgagcgc ttgcacgttt                                       20

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 4
aacaacaaga ccggccacac cctc                                  24

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 5
gaggtggtct ggatggtgta ggtca                                 25

<210> SEQ ID NO 6
<211> LENGTH: 28
<212> TYPE: DNA
<213> ORGANISM: Artificial Sequence
<220> FEATURE:
<223> OTHER INFORMATION: Oligonucleotide primer

```
<400> SEQUENCE: 6
tacaacctca agtggttcct cttcccga                                          28

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 7
gaggtctgga tctgcatgat gcgga                                             25

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 8
aacccttagt atgtatttgt att                                               23

<210> SEQ ID NO 9
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 9
ctccttcaac gttgcggttc tgtcag                                            26

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 10
ttttgcaaag cgaacgattc agatg                                             25

<210> SEQ ID NO 11
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 11
gcgggacaag ccgttttacg ttt                                               23

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 12
gacgggtgat ttatttgatc tgcac                                             25

<210> SEQ ID NO 13
<211> LENGTH: 25
<212> TYPE: DNA
```

-continued

```
<213> ORGANISM: Artificial Sequence
<220> FEATURE:
<223> OTHER INFORMATION: Oligonucleotide primer

<400> SEQUENCE: 13
catctgaatc gttcgctttg caaaa                                               25

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 14
ctacgttcca atggagctcg actgtc                                              26

<210> SEQ ID NO 15
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 15
ggtcaagtgg acacttggtc actca                                               25

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 16
gagtgaagag ataagcaagt caaag                                               25

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 17
catgtatacg taagtttggt gctgg                                               25

<210> SEQ ID NO 18
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 18
aatccacaag attggagcaa acgac                                               25

<210> SEQ ID NO 19
<211> LENGTH: 2593
<212> TYPE: DNA
<213> ORGANISM: Artificial Sequence
<220> FEATURE:
<223> OTHER INFORMATION: 5' flanking sequence of DAS 59122-7.

<400> SEQUENCE: 19
ctgagcgcac aacagcgagt cgcatggcac cggacgacat gagcgagatt tagatcggag         60
```

```
ggtgcggaca tggggcaacc tgcgcagcta acgcagggat ccacacgacc accaacgaag    120
ccaagcccgg gcacgtcccc aggcaggttg ggccctggtt ccaccagcgg atgcatgcag    180
tgaagcgggg acggagagac aagccgaggg cgcgggtggg aatggcgtcc gggaggacga    240
gtggaggaga agaatctaga ggcatcgaga ttcgagaagc cgacggagac aagattcgtg    300 tgggggggaga caaaccgcgg ggctgagcgc cgttgatatg ggatcagacg tgtggataa    360 aaaaagtgac gttgatagaa cgtctggcca gtgaaaaaac aaaacaactc caacaaaata    420
ctttaaaagc tcttataccc taaatgtagg ggatcaaaca cgtctctaca ctatttagca    480
gcgtcctcta aatgatcctc taaatttaga gaacgctact agattctcta tatatagttt    540
ctctaaacga tcttttatcc atttaaatac tttaaataac cggtttaaca aaactaaaat    600
atatacaata catttgagag tatgacaaat acgtatgtat aaaaataaaa aataaaataa    660
tgtattagtc tactttgaat cttctttcct tcataatata atgatgtata gctctcatgt    720
gcgttgagaa aaaagttaga gctagacgtt taatgtgtag tgacagtctt cgacgaaatc    780
tccctaatga gatgaattac tggaggttcc atcagaaagt cccctgaaaa gaggcattta    840
tttagtttag tcagcaattt ctgggaacac aaatattctt ttgttatcac cactattaaa    900
aatctatggt tataacttat aataacatga aaaaataatt tagcatccca tatatataaa    960
aactgaagga agccatatat actaacataa gttaggagaa actaagaagg ttgtgcaaag   1020
cttgcactgc tccaaaatac tgcaaacaac cactctcctc taccaaccaa agaaactcat   1080
gtactccctc cgttcttttt tatttgtcgc attttagttt aaaaatgaac tagcagtcga   1140
caaatattcg agaacagata tagtatatac taacataact taggagatac taagaaagtt   1200
gcgcagagct ttcactgttc caaattactg caaagcctct cccctctgcc agtacatcta   1260
cgagatgttt cagttaaaca aagattcaga caagtgatga gccacttctt gtcatagatt   1320
gtgtggtcaa ccaacccatt gatgccacgg ttttttgtgca tccatgcttt tgtattaaaa   1380
catcagttat gtttaccatg tccgatatgc tctacataat gacaatcaac ttggtgttca   1440
ttatatttac aatgttagga atttcaatag ctacgaacac ttcaatagaa gtgccttgt    1500 gggatcacct taatgtgttg ttgatgtaag gagaagaatc ttaatttact cttgctaaat   1560
ttgaactaca caaaccact gcactgagga ttgtcctaat aaaattactgc tcatacacgt   1620 tagcatctgt tcagatactg agctaatccc taggattaaa ggatttgtaa aagatatgcc   1680
caatcattca ttttagttat ttatttctta gttatccact tgaagattta catacatttg   1740
aaataaattt cttagaggta aagtgaaaat cagttattta aatacatttt agttatttat   1800
tttcttcttt ttcctaattt ttccttgtat ttgaagtctg aaaagataac tttgccctta   1860
tacatatttt atcttctacg tacgcatctg aacaacgtct ctttgtcccc tgatcgtgca   1920
gcaattagtg ctatgaatcg cgtttaagcg ctgcaaaatc atggctgggg cttcgtcctc   1980
gagtcgtcct gctgctcgat gtcacctcga gtcccgcacc gacctcagtg cttgttcttg   2040
ttggagccac ctctctcgga cgatcgccaa agacggataa ggccgaagcc gtcacttcag   2100
accgcgctca tgcgccgtag cagactccta catagcaggg ccagggtatg tggacctttg   2160
caagtttagg attggaacca gcgaccagaa tccacaagat tggagcaaac gaccaaaaat   2220
tcacaaggat tggcggctga cattgccagc gcgggatcgc atgcggcggc ggcggccggg   2280
gcgagcacgg gagcaggcga cagtcgagct ccattggaac gtagaaatac ttaagggcaa   2340
ggtctccaaa tacttgaaaa aataggaaaa agaagaaaat acatgaaatg atattgaaat   2400
caattggaag atgttatgaa tcttgttttt gcaaagcgaa cgattcagat ggcaaaacta   2460
```

-continued

```
tgaatctttt tgtttgaagt cccaaatata aaattttctc gtactcacca acattggtgc      2520
gcacctgtga ttggctcata aaaattcttg gagggacgga agaaagagtg aagggataag      2580
caagtaaaag cgc                                                        2593
```

<210> SEQ ID NO 20
<211> LENGTH: 1986
<212> TYPE: DNA
<213> ORGANISM: Artificial Sequence
<220> FEATURE:
<223> OTHER INFORMATION: 3' flanking sequence of DAS 59122-7.

<400> SEQUENCE: 20

```
ttcccttcta tggtcccgtt tgtttatcct ctaaattata taatccagct taaataagtt        60
aagagacaaa caacaacac agattattaa atagattatg taatctagat acctagatta       120
tgtaatccat aagtagaata tcaggtgctt atataatcta tgagctcgat tatataatct       180
taaaagaaaa caaacagagc ccctataaaa agggtcaag tggacacttg gtcactcatt       240
taatccctcc ctctcctctt ttatccctct ttttggtgta ttcaccaata gtggtgtgca       300
cctgtgattg gctcgtaaaa attcttggac ggatggaaga gtgaagagat aagcaagtca       360
aagaaaagta acaacgaagc ttcatcagct acaaattttg gcccaactgg ttgcaccagc       420
accaaactta cgtatacatg attatctctg tttccctcat ttcgaagaaa aaacgggtt       480 tcaaacccca ctgctttcag gagtaaaaaa agataataat ctgaaacatt gcttccacct       540
tggcccttat ttggttacgt tgcaattcac cccaatccac atgtggattg agatggattg       600
cagtgtagct agacaaaccc ttaggccctg tttgcatagg aatacaccag gaattattcc       660
agctaatcaa aatttatata atgagagaaa acaattcgga taggaattgt tccaggactt       720
cattctgcag taaccgaacg gcccttaat ccaccccaat acacgtggat tggagtggat       780
tgaggtacag ccaaacaagg cctaagtgca gatcaaataa atcacccgtc atattcttct       840
acctacaaaa acagcaataa acacctgaat gaagttctaa tttgcacagt gtaggtagga       900
tgaaaatagt tacctcctca tggtcagtaa ctcttggcac acaacttcac atgtaatcga       960
tgtaccactt ggctcttgcc tgaaacccaa tacatctta gcataagaat aatattatga      1020
tggcaaggca tgatcaccag cactccttta ttgtttagta agtctatcac tccccaaaac      1080
aattcaaatg aacagagatg cattgccccc aatgaattct atttcaatta gccggaaaat      1140
tctacttcat cagaagcatc caaattgcca gcatccctac tagactgacc atgaccaggc      1200
tgccgcagat gcctcttttt ctgtcctctc ctctttgcct tgagtttctc ttcaagatcc      1260
ctcaccccac gtctcttata catcttaaag ctaacatgtc tctcctccgc catcttccta      1320
accttctcag taatctcagc agcaatctga cggttgtaca acttcttcag ccccttcatc      1380
aactttgcaa atgtgtcagg ctgtggcatc agtcctgcct ctagcatgtc taagcaatac      1440
aggcaggcct ccttgacatg tttcttcgca acagtgcat gaatccagat agtccatgca      1500
ctcacattga gctcacagcc tttgctcaca atacatttcc aaacatcctt tgcaagctca      1560
agtttctcat ctctgaccaa cgcattgagg aggtccttca gcaccccata ttgcggtacc      1620
acaaagagcc ccctcccaac catgtcttta aaataactac atgcctcaat cagcaaaccc      1680
tgcccaacaa ggccactcac cacgatagca aatgtatcga ccacaggact gagcccagca      1740
ctttccatct cattccacaa tgtcatggct tgcttggtct ccccaagcct gcaggccaac      1800
cgaatcacca cattgtatat cttgagatct ggtggacacc ggcactcccg catcctctcc      1860
atcagctcca agcactcctc aagctgctcc ttcttctcgt gtgctacaaa gaaaccatgg      1920
```

```
tacacggcag cgtccacccg caggccatcc ctcgacatag catccaagaa ctcgtaccccc   1980 tgggat                                                               1986

<210> SEQ ID NO 21
<211> LENGTH: 3594
<212> TYPE: DNA
<213> ORGANISM: Artificial Sequence
<220> FEATURE:
<223> OTHER INFORMATION: Sequence that represents part of the PHI17662A
      insert as well as flanking sequence 5' to the
      insert.

<400> SEQUENCE: 21
ctgagcgcac aacagcgagt cgcatggcac cggacgacat gagcgagatt tagatcggag     60
ggtgcggaca tggggcaacc tgcgcagcta acgcagggat ccacacgacc accaacgaag    120
ccaagcccgg gcacgtcccc aggcaggttg ggccctggtt ccaccagcgg atgcatgcag    180
tgaagcgggg acgagagac aagccgaggg cgcgggtggg aatggcgtcc gggaggacga    240
gtggaggaga agaatctaga ggcatcgaga ttcgagaagc cgacggagac aagattcgtg    300 tgggggggaga caaaccgcgg ggctgagcgc cgttgatatg ggatcagacg gtgtggataa    360
aaaaagtgac gttgatagaa cgtctggcca gtgaaaaaac aaaacaactc caacaaaata    420
ctttaaaagc tcttataccc taaatgtagg ggatcaaaca cgtctctaca ctatttagca    480
gcgtcctcta aatgatcctc taaatttaga gaacgctact agattctcta tatatagttt    540
ctctaaacga tcttttatcc atttaaatac tttaaataac cggtttaaca aaactaaaat    600
atatacaata catttgagag tatgacaaat acgtatgtat aaaaataaaa aataaaataa    660
tgtattagtc tactttgaat cttctttttct tcataatata atgatgtata gctctcatgt    720
gcgttgagaa aaaagttaga gctagacgtt taatgtgtag tgacagtctt cgacgaaatc    780
tccctaatga gatgaattac tggaggttcc atcagaaagt cccctgaaaa gaggcattta    840
tttagtttag tcagcaattt ctgggaacac aaatattctt ttgttatcac cactattaaa    900
aatctatggt tataacttat aataacatga aaaataatt tagcatccca tatatataaa    960
aactgaagga agccatatat actaacataa gttaggagaa actaagaagg ttgtgcaaag   1020
cttgcactgc tccaaaatac tgcaaacaac cactctcctc taccaaccaa agaaactcat   1080
gtactccctc cgttctttt tatttgtcgc attttagttt aaaaatgaac tagcagtcga   1140
caaatattcg agaacagata tagtatatac taacataact taggagatac taagaaagtt   1200
gcgcagagct ttcactgttc caaattactg caaagcctct cccctctgcc agtacatcta   1260
cgagatgttt cagttaaaca aagattcaga caagtgatga gccacttctt gtcatagatt   1320
gtgtggtcaa ccaacccatt gatgccacg ttttttgtgca tccatgcttt tgtattaaaa    1380
catcagttat gtttaccatg tccgatatgc tctacataat gacaatcaac ttggtgttca   1440
ttatatttac aatgttagga attttcaatag ctacgaacac ttcaatagaa gtgcctttgt   1500
gggatcacct taatgtgttg ttgatgtaag gagaagaatc ttaatttact cttgctaaat   1560
ttgaactaca caaaaccact gcactgagga ttgtcctaat aaattactgc tcatacacgt   1620
tagcatctgt tcagatactg agctaatccc taggattaaa ggatttgtaa aagatatgcc   1680
caatcattca ttttagttat ttatttctta gttatccact tgaagattta catacatttg   1740
aaataaattt cttagaggta aagtgaaaat cagttatta aatacatttt agttatttat   1800
tttcttcttt ttcctaattt ttccttgtat ttgaagtctg aaaagataac tttgcccta   1860 tacatatttt atcttctacg tacgcatctg aacaacgtct ctttgtcccc tgatcgtgca   1920
```

```
gcaattagtg ctatgaatcg cgtttaagcg ctgcaaaatc atggctgggg cttcgtcctc    1980
gagtcgtcct gctgctcgat gtcacctcga gtcccgcacc gacctcagtg cttgttcttg    2040
ttggagccac ctctctcgga cgatcgccaa agacggataa ggccgaagcc gtcacttcag    2100
accgcgctca tgcgccgtag cagactccta catagcaggg ccagggtatg tggaccttttg   2160 caagtttagg attggaacca gcgaccagaa tccacaagat tggagcaaac gaccaaaaat    2220
tcacaaggat tggcggctga cattgccagc gcgggatcgc atgcggcggc ggcggccggg    2280
gcgagcacgg gagcaggcga cagtcgagct ccattggaac gtagaaatac ttaagggcaa    2340
ggtctccaaa tacttgaaaa aataggaaaa agaagaaaat acatgaaatg atattgaaat    2400
caattggaag atgttatgaa tcttgttttt gcaaagcgaa cgattcagat ggcaaaacta    2460
tgaatctttt tgtttgaagt cccaaatata aatttttctc gtactcacca acattggtgc    2520
gcacctgtga ttggctcata aaaattcttg gagggacgga agaaagagtg aagggataag    2580
caagtaaaag cgctcaaaca ctgatagttt aaactgaagg cgggaaacga caatctgatc    2640
atgagcggag aattaaggga gtcacgttat gaccccgcc gatgacgcgg gacaagccgt     2700
tttacgtttg gaactgacag aaccgcaacg ttgaaggagc cactcagcaa gcttactagt    2760
agcgctgttt aaacgctctt caactggaag agcggttacc cggaccgaag cttgcatgcc    2820
tgcagtgcag cgtgacccgg tcgtgcccct ctctagagat aatgagcatt gcatgtctaa    2880
gttataaaaa attaccacat atttttttg tcacacttgt ttgaagtgca gtttatctat     2940
ctttatacat atatttaaac tttactctac gaataatata atctatagta ctacaataat    3000
atcagtgttt tagagaatca tataaatgaa cagttagaca tggtctaaag gacaattgag    3060
tattttgaca acaggactct acagttttat cttttagtg tgcatgtgtt ctcctttttt     3120
tttgcaaata gcttcaccta tataatactt catccatttt attagtacat ccatttaggg    3180
tttagggtta atggttttta tagactaatt tttttagtac atctatttta ttctatttta    3240
gcctctaaat taagaaaact aaaactctat tttagttttt ttatttaata atttagatat    3300
aaaatagaat aaaataaagt gactaaaaat taaacaaata ccctttaaga aattaaaaaa    3360
actaaggaaa cattttttctt gtttcgagta gataatgcca gcctgttaaa cgccgtcgac    3420
gagtctaacg gacaccaacc agcgaaccag cagcgtcgcg tcgggccaag cgaagcagac    3480
ggcacggcat ctctgtcgct gcctctggac ccctctcgag agttccgctc caccgttgga    3540
cttgctccgc tgtcggcatc cagaaattgc gtggcggagc ggcagacgtg agcc          3594
```

<210> SEQ ID NO 22
<211> LENGTH: 2987
<212> TYPE: DNA
<213> ORGANISM: Artificial Sequence
<220> FEATURE:
<223> OTHER INFORMATION: Sequence that represents part of the PHI17662A insert as well as flanking sequence 3' to the insert.

<400> SEQUENCE: 22

```
ctccggagag gagaccagtt gagattaggc cagctacagc agctgatatg gccgcggttt    60
gtgatatcgt taaccattac attgagacgt ctacagtgaa ctttaggaca gagccacaaa    120
caccacaaga gtggattgat gatctagaga ggttgcaaga tagataccct tggttggttg    180
ctgaggttga gggtgttgtg ctggtattg cttacgctgg gccctggaag ctaggaacg     240 cttacgattg gacagttgag agtactgttt acgtgtcaca taggcatcaa aggttgggcc    300
taggatccac attgtacaca catttgctta agtctatgga ggcgcaaggt tttaagtctg    360
```

```
tggttgctgt tataggcctt ccaaacgatc catctgttag gttgcatgag gctttgggat    420
acacagcccg gggtacattg cgcgcagctg gatacaagca tggtggatgg catgatgttg    480 gttttttggca agggattttt gagttgccag ctcctccaag gccagttagg ccagttaccc    540
agatctgagt cgacctgcag gcatgcccgc tgaaatcacc agtctctctc tacaaatcta    600
tctctctcta taataatgtg tgagtagttc ccagataagg gaattagggt cttataggg     660 tttcgctcat gtgttgagca tataagaaac ccttagtatg tatttgtatt tgtaaaatac    720
ttctatcaat aaaatttcta attcctaaaa ccaaaatcca gggcgagctc ggtacccggg    780
gatcctctag agtcgacctg caggcatgcc cgcggatatc gatgggcccc ggccgaagct    840
tcggtccggg ccatcgtggc ctcttgctct tcaggatgaa gagctatgtt taaacgtgca    900
agcgctcaat tcgccctata gtgagtcgta ttacaatcgt acgcaattca gtacattaaa    960
aacgtccgca atgtgttatt aagttgtcta agcgtcaatt tttcccttct atggtcccgt   1020
ttgtttatcc tctaaattat ataatccagc ttaataagt taagagacaa acaaacaaca    1080
cagattatta aatagattat gtaatctaga tacctagatt atgtaatcca taagtagaat   1140
atcaggtgct tatataatct atgagctcga ttatataatc ttaaaagaaa acaaacagag   1200
cccctataaa aaggggtcaa gtggacactt ggtcactcat ttaatccctc cctctcctct   1260
tttatccctc tttttggtgt attcaccaat agtggtgtgc acctgtgatt ggctcgtaaa   1320
aattcttgga cggatggaag agtgaagaga taagcaagtc aaagaaaagt aacaacgaag   1380
cttcatcagc tacaaatttt ggcccaactg gttgcaccag caccaaactt acgtatacat   1440
gattatctct gtttccctca tttcgaagaa aaaaacgggt ttcaaaaccc actgctttca   1500
ggagtaaaaa aagataataa tctgaaacat tgcttccacc ttggcccctta tttggttacg   1560 ttgcaattca ccccaatcca catgtggatt gagatggatt gcagtgtagc tagacaaacc   1620
cttaggccct gtttgcatag gaatacacca ggaattattc cagctaatca aaatttatat   1680
aaatgagaga acaattcgg ataggaattg ttccaggact tcattctgca gtaaccgaac    1740
ggccccttaa tccaccccaa tacacgtgga ttggagtgga ttgaggtaca gccaaacaag   1800
gcctaagtgc agatcaaata aatcacccgt catattcttc tacctacaaa acagcaata    1860 aacacctgaa tgaagttcta atttgcacag tgtaggtagg atgaaaatag ttacctcctc   1920
atggtcagta actcttggca cacaacttca catgtaatcg atgtaccact tggctcttgc   1980
ctgaaaccca atacatcttt agcataagaa taatattatg atggcaaggc atgatcacca   2040
gcactccttt attgtttagt aagtctatca ctccccaaaa caattcaaat gaacagagat   2100
gcattgcccc caatgaattc tatttcaatt agccggaaaa ttctacttca tcagaagcat   2160
ccaaattgcc agcatcccta ctagactgac catgaccagg ctgccgcaga tgcctctttt   2220
tctgtcctct cctctttgcc ttgagttct cttcaagatc cctcacccca cgtctcttat    2280
acatcttaaa gctaacatgt ctctcctccg ccatcttcct aaccttctca gtaatctcag   2340
cagcaatctg acggttgtac aacttcttca gccccttcat caactttgca aatgtgtcag   2400
gctgtggcat cagtcctgcc tctagcatgt ctaagcaata caggcaggcc tccttgacat   2460
gtttcttcgc aaacagtgca tgaatccaga tagtccatgc actcacattg agctcacagc   2520 cttttgctcac aatacatttc caaacatcct ttgcaagctc aagtttctca tctctgacca   2580
acgcattgag gaggtccttc agcaccccat attgcggtac cacaaagagc cccctcccaa   2640
ccatgtcttt aaaataacta catgcctcaa tcagcaaacc ctgcccaaca aggccactca   2700
ccacgatagc aaatgtatcg accacaggac tgagcccagc actttccatc tcattccaca   2760
```

-continued

| | |
|---|---|
| atgtcatggc ttgcttggtc tccccaagcc tgcaggccaa ccgaatcacc acattgtata | 2820 |
| tcttgagatc tggtggacac cggcactccc gcatcctctc catcagctcc aagcactcct | 2880 |
| caagctgctc cttcttctcg tgtgctacaa agaaaccatg gtacacggca gcgtccaccc | 2940 |
| gcaggccatc cctcgacata gcatccaaga actcgtaccc ctgggat | 2987 |

<210> SEQ ID NO 23
<211> LENGTH: 11922
<212> TYPE: DNA
<213> ORGANISM: Artificial Sequence
<220> FEATURE:
<223> OTHER INFORMATION: The sequence represents the complete sequence
of the insert and flanking regions of event DAS
59122-7.

<400> SEQUENCE: 23

| | |
|---|---|
| ctgagcgcac aacagcgagt cgcatggcac cggacgacat gagcgagatt tagatcggag | 60 |
| ggtgcggaca tggggcaacc tgcgcagcta acgcagggat ccacacgacc accaacgaag | 120 |
| ccaagcccgg gcacgtcccc aggcaggttg ggccctggtt ccaccagcgg atgcatgcag | 180 |
| tgaagcgggg acgagagac aagccgaggg cgcgggtggg aatggcgtcc gggaggacga | 240 |
| gtggaggaga agaatctaga ggcatcgaga ttcgagaagc cgacggagac aagattcgtg | 300 |
| tgggggagaga caaccgcgg ggctgagcgc cgttgatatg ggatcagacg gtgtggataa | 360 |
| aaaaagtgac gttgatagaa cgtctggcca gtgaaaaaac aaaacaactc caacaaaata | 420 |
| ctttaaaagc tcttataccc taaatgtagg ggatcaaaca cgtctctaca ctatttagca | 480 |
| gcgtcctcta aatgatcctc taaatttaga gaacgctact agattctcta tatatagttt | 540 |
| ctctaaacga tcttttatcc atttaaatac tttaaataac cggtttaaca aaactaaaat | 600 |
| atatacaata catttgagag tatgacaaat acgtatgtat aaaaataaaa aataaaataa | 660 |
| tgtattagtc tactttgaat cttcttttct tcataatata atgatgtata gctctcatgt | 720 |
| gcgttgagaa aaaagttaga gctagacgtt taatgtgtag tgacagtctt cgacgaaatc | 780 |
| tccctaatga gatgaattac tggaggttcc atcagaaagt cccctgaaaa gaggcattta | 840 |
| tttagtttag tcagcaattt ctgggaacac aaatattctt ttgttatcac cactattaaa | 900 |
| aatctatggt tataacttat aataacatga aaaataatt tagcatccca tatatataaa | 960 |
| aactgaagga agccatatat actaacataa gttaggagaa actaagaagg ttgtgcaaag | 1020 |
| cttgcactgc tccaaaatac tgcaaacaac cactctcctc taccaaccaa agaaactcat | 1080 |
| gtactccctc cgttcttttt tatttgtcgc atttttagttt aaaaatgaac tagcagtcga | 1140 |
| caaatattcg agaacagata tagtatatac taacataact taggagatac taagaaagtt | 1200 |
| gcgcagagct ttcactgttc caaattactg caaagcctct cccctctgcc agtacatcta | 1260 |
| cgagatgttt cagttaaaca aagattcaga caagtgatga gccacttctt gtcatagatt | 1320 |
| gtgtggtcaa ccaacccatt gatgccacgg ttttgtgca tccatgcttt tgtattaaaa | 1380 |
| catcagttat gtttaccatg tccgatatgc tctacataat gacaatcaac ttggtgttca | 1440 |
| ttatatttac aatgttagga atttcaatag ctacgaacac ttcaatagaa gtgcctttgt | 1500 |
| gggatcacct taatgtgttg ttgatgtaag gagaagaatc ttaatttact cttgctaaat | 1560 |
| ttgaactaca caaaaccact gcactgagga ttgtcctaat aaattactgc tcatacacgt | 1620 |
| tagcatctgt tcagatactg agctaatccc taggattaaa ggatttgtaa aagatatgcc | 1680 |
| caatcattca ttttagttat ttatttctta gttatccact tgaagattta catacatttg | 1740 |
| aaataaattt cttagaggta aagtgaaaat cagttatttta aatacatttt agttatttat | 1800 |

```
tttcttctttt ttcctaatttt ttccttgtat ttgaagtctg aaaagataac tttgccctta    1860
tacatatttt atcttctacg tacgcatctg aacaacgtct ctttgtcccc tgatcgtgca    1920
gcaattagtg ctatgaatcg cgtttaagcg ctgcaaaatc atggctgggg cttcgtcctc    1980
gagtcgtcct gctgctcgat gtcacctcga gtcccgcacc gacctcagtg cttgttcttg    2040
ttggagccac ctctctcgga cgatcgccaa agacggataa ggccgaagcc gtcacttcag    2100
accgcgctca tgcgccgtag cagactccta catagcaggg ccagggtatg tggacctttg    2160
caagtttagg attggaacca gcgaccagaa tccacaagat tggagcaaac gaccaaaaat    2220
tcacaaggat tggcggctga cattgccagc gcgggatcgc atgcggcggc ggcggccggg    2280
gcgagcacgg gagcaggcga cagtcgagct ccattggaac gtagaaatac ttaagggcaa    2340
ggtctccaaa tacttgaaaa aataggaaaa agaagaaaat acatgaaatg atattgaaat    2400
caattggaag atgttatgaa tcttgttttt gcaaagcgaa cgattcagat ggcaaaacta    2460
tgaatctttt tgtttgaagt cccaaatata aaatttctc gtactcacca acattggtgc    2520
gcacctgtga ttggctcata aaaattcttg gagggacgga agaaagagtg aagggataag    2580
caagtaaaag cgctcaaaca ctgatagttt aaactgaagg cgggaaacga caatctgatc    2640
atgagcggag aattaaggga gtcacgttat gaccccgcc gatgacgcgg gacaagccgt    2700
tttacgtttg gaactgacag aaccgcaacg ttgaaggagc cactcagcaa gcttactagt    2760
agcgctgttt aaacgctctt caactggaag agcggttacc cggaccgaag cttgcatgcc    2820
tgcagtgcag cgtgacccgg tcgtgcccct ctctagagat aatgagcatt gcatgtctaa    2880
gttataaaaa attaccacat attttttttg tcacacttgt ttgaagtgca gtttatctat    2940
ctttatacat atatttaaac tttactctac gaataatata atctatagta ctacaataat    3000
atcagtgttt tagagaatca tataaatgaa cagttagaca tggtctaaag gacaattgag    3060 tatttttgaca acaggactct acagttttat cttttagtg tgcatgtgtt ctccttttt    3120 tttgcaaata gcttcaccta tataatactt catccatttt attagtacat ccatttaggg    3180
tttagggtta atggtttta tagactaatt tttttagtac atctattta ttctattta    3240 gcctctaaat taagaaaact aaaactctat tttagttttt ttatttaata atttagatat    3300
aaaatagaat aaaataaagt gactaaaaat taaacaaata ccctttaaga aattaaaaaa    3360
actaaggaaa cattttctt gtttcgagta gataatgcca gcctgttaaa cgccgtcgac    3420
gagtctaacg gacaccaacc agcgaaccag cagcgtcgcg tcgggccaag cgaagcagac    3480
ggcacggcat ctctgtcgct gcctctggac ccctctcgag agttccgctc caccgttgga    3540
cttgctccgc tgtcggcatc cagaaattgc gtggcggagc ggcagacgtg agccggcacg    3600
gcaggcggcc tcctcctcct ctcacggcac cggcagctac gggggattcc tttcccaccg    3660
ctccttcgct ttcccttcct cgcccgccgt aataaataga caccccctcc acaccctctt    3720
tccccaacct cgtgttgttc ggagcgcaca cacacacaac cagatctccc ccaaatccac    3780
ccgtcggcac ctccgcttca aggtacgccg ctcgtcctcc cccccccccc ctctctacct    3840
tctctagatc ggcgttccgg tccatggtta gggcccggta gttctacttc tgttcatgtt    3900
tgtgttagat ccgtgtttgt gttagatccg tgctgctagc gttcgtacac ggatgcgacc    3960
tgtacgtcag acacgttctg attgctaact tgccagtgtt tctctttggg gaatcctggg    4020
atggctctag ccgttccgca gacgggatcg atttcatgat tttttttgtt tcgttgcata    4080
gggtttggtt tgcccttttc ctttatttca atatatgccg tgcacttgtt tgtcgggtca    4140
tcttttcatg cttttttttg tcttggttgt gatgatgtgg tctggttggg cggtcgttct    4200
```

```
agatcggagt agaattctgt ttcaaactac ctggtggatt tattaattt  ggatctgtat    4260
gtgtgtgcca tacatattca tagttacgaa ttgaagatga tggatggaaa tatcgatcta    4320
ggataggtat acatgttgat gcgggtttta ctgatgcata tacagagatg ctttttgttc    4380
gcttggttgt gatgatgtgg tgtggttggg cggtcgttca ttcgttctag atcggagtag    4440
aatactgttt caaactacct ggtgtattta ttaattttgg aactgtatgt gtgtgtcata    4500
catcttcata gttacgagtt taagatggat ggaaatatcg atgtaggata ggtatacatg    4560
ttgatgtggg ttttactgat gcatatacat gatggcatat gcagcatcta ttcatatgct    4620
ctaaccttga gtacctatct attataataa acaagtatgt tttataatta ttttgatctt    4680
gatatacttg gatgatggca tatgcagcag ctatatgtgg attttttag  ccctgccttc    4740
atacgctatt tatttgcttg gtactgtttc ttttgtcgat gctcaccctg ttgtttggtg    4800
ttacttctgc aggtcgactc tagaggatcc acacgacacc atgtccgccc gcgaggtgca    4860
catcgacgtg aacaacaaga ccggccacac cctccagctg gaggacaaga ccaagctcga    4920
cggcggcagg tggcgcacct ccccgaccaa cgtggccaac gaccagatca agaccttcgt    4980
ggccgaatcc aacggcttca tgaccggcac cgagggcacc atctactact caattaatgg    5040
cgaggccgag atcagcctct acttcgacaa cccgttcgcc ggctccaaca aatacgacgg    5100
ccactccaac aagtcccagt acgagatcat caccccaggc ggctccggca accagtccca    5160
cgtgacctac accatccaga ccacctcctc ccgctacggc acaagtcct  gagtcatgag    5220
tcatgagtca gttaacctag acttgtccat cttctggatt ggccaactta attaatgtat    5280
gaaataaaag gatgcacaca tagtgacatg ctaatcacta taatgtgggc atcaaagttg    5340
tgtgttatgt gtaattacta gttatctgaa taaaagagaa agagatcatc catatttctt    5400
atcctaaatg aatgtcacgt gtcttttataa ttctttgatg aaccagatgc atttcattaa    5460
ccaaatccat atacatataa atattaatca tatataatta atatcaattg ggttagcaaa    5520
acaaatctag tctaggtgtg ttttgcgaat gcggccgcgg accgaattgg ggatctgcat    5580
gaaagaaact gtcgcactgc tgaaccgcac cttgtcactt tcatcgaaca cgacctgtgc    5640
ccaagatgac ggtgctgcgg tctaagtgag gctgaattgc cttggacaga agcggactcc    5700
ctacaattag ttaggccaaa cggtgcatcc atgtgtagct ccgggctcgg gctgtatcgc    5760
catctgcaat agcatccatg gagctcgttc catgtagttg gagatgaacc aatgatcggg    5820
cgtgtggacg tatgttcctg tgtactccga tagtagagta cgtgttagct ctttcatggt    5880
gcaagtgaaa tttgtgttgg tttaattacc cctacgttag ttgcgggaca ggagacacat    5940
catgaattta aaggcgatga tgtcctctcc tgtaatgtta ttcttttgat gtgatgaatc    6000
aaaatgtcat ataaaacatt tgttgctctt tagttaggcc tgatcgtaga acgaaatgct    6060
cgtgtagcgg ggctacgagc ctatgacgca ataacactgg tttgccggcc cggagtcgct    6120
tgacaaaaaa aagcatgtta agtttattta caattcaaaa cctaacatat tatattccct    6180
caaagcaggt tcacgatcac acctgtacct aaaaaaaaca tgaagaatat attactccat    6240
tattatgaga tgaaccactt ggcaagagtg gtaagctata taaaaaaatg aacattatta    6300
cgagatgtta tatgccatta tattgattcg aagatatatg tttctttctc ccacgggcac    6360
ctaacgata  catgataagg ccaaggcaga tcacgggaaa ttattcgaat acatgttacg    6420
ccctattgcc ggaaaaaaaa tgcagggcag gtgttggccg tagcgattta agcacttaag    6480
ctggaggttg ccacacttgg atgcaagcgt ctgaccctte taaaacatcg gcggctttgt    6540
ccgtatccgt atccctatc  cgacatctag ctggccacac gacggggctg ggcagatcgt    6600
```

```
ggatgccggg tcgacgtcga tcgtcagcca tcatagacca atcgaccatc tgttatggat    6660
gcttgctagc tagactagtc agacataaaa tttggatact ttctcccaac tgggagacgg    6720
ggactgatgt gcagctgcac gtgagctaaa ttttteccta taaatatgca tgaaatactg    6780
cattatcttg ccacagccac tgccacagcc agataacaag tgcagctggt agcacgcaac    6840
gcatagctct ggacttgtag ctaggtagcc aaccggatcc acacgacacc atgctcgaca    6900
ccaacaaggt gtacgagatc agcaaccacg ccaacggcct ctacgccgcc acctacctct    6960
ccctcgacga ctccggcgtg tccctcatga acaagaacga cgacgacatc gacgactaca    7020
acctcaagtg gttcctcttc ccgatcgacg acgaccagta catcatcacc tcctacgccg    7080
ccaacaactg caaggtgtgg aacgtgaaca cgacaagat  taatgtgtca acctactcct    7140
ccaccaactc catccagaag tggcagatca aggccaacgg ctcctcctac gtgatccagt    7200
ccgacaacgg caaggtgctc accgccggca ccggccaggc cctcggcctc atccgcctca    7260
ccgacgagtc ctccaacaac ccgaaccagc aatggaacct gacgtccgtg cagaccatcc    7320
agctcccgca gaagccgatc atcgacacca agctcaagga ctacccgaag tactccccga    7380
ccggcaacat cgacaacggc acctccccgc agctcatggg ctggaccctc gtgccgtgca    7440
tcatggtgaa cgacccgaac atcgacaaga cacccagat  caagaccacc ccgtactaca    7500
tcctcaagaa gtaccagtac tggcagaggg ccgtgggctc caacgtcgcg ctccgcccgc    7560
acgagaagaa gtcctacacc tacgagtggg gcaccgagat cgaccagaag accaccatca    7620
tcaacacccT cggcttccag atcaacatcg acagcggcat gaagttcgac atcccggagg    7680
tgggcggcgg taccgacgag atcaagaccc agctcaacga ggagctcaag atcgagtatt    7740
cacatgagac gaagatcatg gagaagtacc aggagcagtc cgagatcgac aacccgaccg    7800
accagtccat gaactccatc ggcttcctca ccatcacctc cctggagctc taccgctaca    7860
acggctccga gatccgcatc atgcagatcc agacctccga caacgacacc tacaacgtga    7920
cctcctaccc gaaccaccag caggccctgc tgctgctgac caaccactcc tacgaggagg    7980
tggaggagat caccaacatc ccgaagtcca ccctcaagaa gctcaagaag tactacttct    8040
gagtcatgag tcatgagtca gttaacctag acttgtccat cttctggatt ggccaactta    8100
attaatgtat gaaataaaag gatgcacaca tagtgacatg ctaatcacta taatgtgggc    8160
atcaaagttg tgtgttatgt gtaattacta gttatctgaa taaaagagaa agagatcatc    8220
catatttctt atcctaaatg aatgtcacgt gtctttataa ttctttgatg aaccagatgc    8280
atttcattaa ccaaatccat atacatataa atattaatca tatataatta atatcaattg    8340
ggttagcaaa acaaatctag tctaggtgtg ttttgcgaat tcccatggag tcaaagattc    8400
aaatagagga cctaacagaa ctcgccgtaa agactggcga acagttcata cagagtctct    8460
tacgactcaa tgacaagaag aaaatcttcg tcaacatggt ggagcacgac acgcttgtct    8520
actccaaaaa tatcaaagat acagtctcag aagaccaaag gcaattgag  acttttcaac    8580 aaagggtaat atccggaaac ctcctcggat tccattgccc agctatctgt cactttattg    8640
tgaagatagt ggaaaaggaa ggtggctcct acaaatgcca tcattgcgat aaaggaaagg    8700
ccatcgttga agatgcctct gccgacagtg gtcccaaaga tggaccccca cccacgagga    8760
gcatcgtgga aaaagaagac gttccaacca cgtcttcaaa gcaagtggat tgatgtgata    8820
tctccactga cgtaagggat gacgcacaat cccactatcc ttcgcaagac ccttcctcta    8880
tataaggaag ttcatttcat ttggagagga cagggtaccc gggggatccac catgtctccg    8940 gagaggagac cagttgagat taggccagct acagcagctg atatggccgc ggtttgtgat    9000
```

-continued

```
atcgttaacc attacattga gacgtctaca gtgaacttta ggacagagcc acaaacacca    9060
caagagtgga ttgatgatct agagaggttg caagatagat acccttggtt ggttgctgag    9120
gttgagggtg ttgtggctgg tattgcttac gctgggccct ggaaggctag aacgcttac    9180 gattggacag ttgagagtac tgtttacgtg tcacataggc atcaaaggtt gggcctagga    9240
tccacattgt acacacattt gcttaagtct atggaggcgc aaggttttaa gtctgtggtt    9300
gctgttatag gccttccaaa cgatccatct gttaggttgc atgaggcttt gggatacaca    9360
gcccggggta cattgcgcgc agctggatac aagcatggtg gatggcatga tgttggtttt    9420
tggcaaaggg atttgagtt gccagctcct ccaaggccag ttaggccagt tacccagatc    9480
tgagtcgacc tgcaggcatg cccgctgaaa tcaccagtct ctctctacaa atctatctct    9540
ctctataata atgtgtgagt agttcccaga taagggaatt agggttctta tagggtttcg    9600
ctcatgtgtt gagcatataa gaaacccctta gtatgtattt gtatttgtaa aatacttcta    9660
tcaataaaat ttctaattcc taaaaccaaa atccagggcg agctcggtac ccggggatcc    9720
tctagagtcg acctgcaggc atgcccgcgg atatcgatgg gccccggccg aagcttcggt    9780
ccgggccatc gtggcctctt gctcttcagg atgaagagct atgtttaaac gtgcaagcgc    9840
tcaattcgcc ctatagtgag tcgtattaca atcgtacgca attcagtaca ttaaaaacgt    9900
ccgcaatgtg ttattaagtt gtctaagcgt caatttttcc cttctatggt cccgtttgtt    9960
tatcctctaa attatataat ccagcttaaa taagttaaga gacaaacaaa caacacagat   10020
tattaaatag attatgtaat ctagatacct agattatgta atccataagt agaatatcag   10080
gtgcttatat aatctatgag ctcgattata taatcttaaa agaaaacaaa cagagcccct   10140
ataaaagggg gtcaagtgga cacttggtca ctcatttaat ccctccctct cctcttttat   10200
ccctcttttt ggtgtattca ccaatagtgg tgtgcacctg tgattggctc gtaaaaattc   10260
ttggacggat ggaagagtga agagataagc aagtcaaaga aaagtaacaa cgaagcttca   10320
tcagctacaa attttggccc aactggttgc accagcacca aacttacgta tacatgatta   10380
tctctgtttc cctcatttcg aagaaaaaaa cgggtttcaa aacccactgc tttcaggagt   10440
aaaaaaagat aataatctga aacattgctt ccaccttggc ccttatttgg ttacgttgca   10500 attcaccccca atccacatgt ggattgagat ggattgcagt gtagctagac aaacccttag   10560
gccctgtttg cataggaata caccaggaat tattccagct aatcaaaatt tatataaatg   10620
agagaaacaa ttcggatagg aattgttcca ggacttcatt ctgcagtaac cgaacggccc   10680
cttaatccac cccaatacac gtggattgga gtggattgag gtacagccaa acaaggccta   10740
agtgcagatc aaataaatca cccgtcatat tcttctacct acaaaaacag caataaacac   10800
ctgaatgaag ttcaatttg cacagtgtag gtaggatgaa aatagttacc tcctcatggt   10860
cagtaactct tggcacacaa cttcacatgt aatcgatgta ccacttggct cttgcctgaa   10920
acccaataca tctttagcat aagaataata ttatgatggc aaggcatgat caccagcact   10980
cctttattgt ttagtaagtc tatcactccc caaaacaatt caaatgaaca gagatgcatt   11040
gcccccaatg aattctatttt caattagccg gaaaattcta cttcatcaga agcatccaaa   11100
ttgccagcat ccctactaga ctgaccatga ccaggctgcc gcagatgcct ctttttctgt   11160
cctctcctct ttgccttgag tttctcttca agatccctca ccccacgtct cttatacatc   11220
ttaaagctaa catgtctctc ctccgccatc ttcctaacct tctcagtaat ctcagcagca   11280
atctgacggt tgtacaactt cttcagcccc ttcatcaact ttgcaaatgt gtcaggctgt   11340
ggcatcagtc ctgcctctag catgtctaag caatacaggc aggcctcctt gacatgtttc   11400
```

-continued

```
ttcgcaaaca gtgcatgaat ccagatagtc catgcactca cattgagctc acagcctttg    11460
ctcacaatac atttccaaac atcctttgca agctcaagtt tctcatctct gaccaacgca    11520
ttgaggaggt ccttcagcac cccatattgc ggtaccacaa agagcccct cccaaccatg     11580 tctttaaaat aactacatgc ctcaatcagc aaaccctgcc caacaaggcc actcaccacg    11640
atagcaaatg tatcgaccac aggactgagc ccagcacttt ccatctcatt ccacaatgtc    11700
atggcttgct tggtctcccc aagcctgcag gccaaccgaa tcaccacatt gtatatcttg    11760
agatctggtg gacaccggca ctcccgcatc ctctccatca gctccaagca ctcctcaagc    11820
tgctccttct tctcgtgtgc tacaaagaaa ccatggtaca cggcagcgtc cacccgcagg    11880
ccatccctcg acatagcatc aagaactcg taccccctggg at                      11922
```

<210> SEQ ID NO 24
<211> LENGTH: 7390
<212> TYPE: DNA
<213> ORGANISM: Artificial Sequence
<220> FEATURE:
<223> OTHER INFORMATION: This sequence represents the DNA molecule used
      to transform maize line DAS59122-7 and represents
      insert PHI 17662A.
<221> NAME/KEY: misc_feature
<222> LOCATION: (1)...(25)
<223> OTHER INFORMATION: T-DNA right border
<221> NAME/KEY: misc_feature
<222> LOCATION: (7366)...(7390)
<223> OTHER INFORMATION: T-DNA left border

<400> SEQUENCE: 24

```
gtttacccgc caatatatcc tgtcaaacac tgatagttta aactgaaggc gggaaacgac      60
aatctgatca tgagcggaga attaagggag tcacgttatg accccgccg atgacgcggg     120 acaagccgtt ttacgtttgg aactgacaga accgcaacgt tgaaggagcc actcagcaag    180
cttactagta gcgctgttta aacgctcttc aactggaaga gcggttaccc ggaccgaagc    240
ttgcatgcct gcagtgcagc gtgacccggt cgtgccctc tctagagata atgagcattg     300
catgtctaag ttataaaaaa ttaccacata ttttttttgt cacacttgtt tgaagtgcag    360
tttatctatc tttatacata tatttaaact ttactctacg aataatataa tctatagtac    420
tacaataata tcagtgtttt agagaatcat ataaatgaac agttagacat ggtctaaagg    480
acaattgagt attttgacaa caggactcta cagttttatc tttttagtgt gcatgtgttc    540
tccttttttt ttgcaaatag cttcacctat ataatacttc atccattta ttagtacatc     600 catttagggt ttagggttaa tggttttat agactaattt ttttagtaca tctattttat    660
tctattttag cctctaaatt aagaaaacta aaactctatt ttagtttttt tatttaataa    720
tttagatata aaatagaata aaataaagtg actaaaaatt aaacaaatac cctttaagaa    780
attaaaaaaa ctaaggaaac attttttcttg tttcgagtag ataatgccag cctgttaaac    840
gccgtcgacg agtctaacgg acaccaacca gcgaaccagc agcgtcgcgt cgggccaagc    900
gaagcagacg gcacggcatc tctgtcgctg cctctggacc cctctcgaga gttccgctcc    960
accgttggac ttgctccgct gtcggcatcc agaaattgcg tggcggagcg gcagacgtga    1020
gccggcacgg caggcggcct cctcctcctc tcacggcacc ggcagctacg ggggattcct    1080
ttcccaccgc tccttcgctt tcccttcctc gcccgccgta ataaatagac ccccctcca     1140 caccctcttt ccccaacctc gtgttgttcg agcgcacac acacacaacc agatctcccc    1200
caaatccacc cgtcgcacc tccgcttcaa ggtacgccgc tcgtcctccc cccccccccc    1260
tctctacctt ctctagatcg gcgttccggt ccatggttag ggcccggtag ttctacttct    1320
```

```
gttcatgttt gtgttagatc cgtgtttgtg ttagatccgt gctgctagcg ttcgtacacg    1380
gatgcgacct gtacgtcaga cacgttctga ttgctaactt gccagtgttt ctctttgggg    1440
aatcctggga tggctctagc cgttccgcag acgggatcga tttcatgatt ttttttgttt    1500
cgttgcatag ggtttggttt gcccttttcc tttatttcaa tatatgccgt gcacttgttt    1560
gtcgggtcat cttttcatgc ttttttttgt cttggttgtg atgatgtggt ctggttgggc    1620
ggtcgttcta gatcggagta gaattctgtt tcaaactacc tggtggattt attaattttg    1680
gatctgtatg tgtgtgccat acatattcat agttacgaat tgaagatgat ggatggaaat    1740
atcgatctag gataggtata catgttgatg cgggttttac tgatgcatat acagagatgc    1800 ttttgttcg cttggttgtg atgatgtggt gtggttgggc ggtcgttcat tcgttctaga     1860
tcggagtaga atactgtttc aaactacctg gtgtatttat taattttgga actgtatgtg    1920
tgtgtcatac atcttcatag ttacgagttt aagatggatg gaaatatcga tgtaggatag    1980
gtatacatgt tgatgtgggt tttactgatg catatacatg atggcatatg cagcatctat    2040
tcatatgctc taaccttgag tacctatcta ttataataaa caagtatgtt ttataattat    2100
tttgatcttg atatacttgg atgatggcat atgcagcagc tatatgtgga ttttttttagc   2160 cctgccttca tacgctattt atttgcttgg tactgtttct tttgtcgatg ctcaccctgt    2220
tgtttggtgt tacttctgca ggtcgactct agaggatcca cacgacacca tgtccgcccg    2280
cgaggtgcac atcgacgtga acaacaagac cggccacacc ctccagctgg aggacaagac    2340
caagctcgac ggcggcaggt ggcgcacctc cccgaccaac gtggccaacg accagatcaa    2400
gaccttcgtg gccgaatcca acggcttcat gaccggcacc gagggcacca tctactactc    2460
aattaatggc gaggccgaga tcagcctcta cttcgacaac ccgttcgccg gctccaacaa    2520
atacgacggc cactccaaca gtcccagta cgagatcatc acccagggcg gctccggcaa    2580
ccagtcccac gtgacctaca ccatccagac cacctcctcc cgctacgcc acaagtcctg    2640 agtcatgagt catgagtcag ttaacctaga cttgtccatc ttctggattg gccaacttaa    2700
ttaatgtatg aaataaaagg atgcacacat agtgacatgc taatcactat aatgtgggca    2760
tcaaagttgt gtgttatgtg taattactag ttatctgaat aaaagagaaa gagatcatcc    2820
atatttctta tcctaaatga atgtcacgtg tctttataat tctttgatga accagatgca    2880
tttcattaac caaatccata tacatataaa tattaatcat atataattaa tatcaattgg    2940
gttagcaaaa caaatctagt ctaggtgtgt tttgcgaatg cggccgcgga ccgaattggg    3000
gatctgcatg aaagaaactg tcgcactgct gaaccgcacc ttgtcacttt catcgaacac    3060
gacctgtgcc caagatgacg gtgctgcggt ctaagtgagg ctgaattgcc ttggacagaa    3120
gcggactccc tacaattagt taggccaaac ggtgcatcca tgtgtagctc cgggctcggg    3180
ctgtatcgcc atctgcaata gcatccatgg agctcgttcc atgtagttgg agatgaacca    3240
atgatcgggc gtgtggacgt atgttcctgt gtactccgat agtagagtac gtgttagctc    3300
tttcatggtg caagtgaaat ttgtgttggt ttaattaccc ctacgttagt tgcgggacag    3360
gagacacatc atgaatttaa aggcgatgat gtcctctcct gtaatgttat tcttttgatg    3420
tgatgaatca aaatgtcata taaaacattt gttgctcttt agttaggcct gatcgtagaa    3480
cgaaatgctc gtgtagcggg gctacgagcc tatgacgcaa taacactggt ttgccggccc    3540
ggagtcgctt gacaaaaaaa agcatgttaa gtttatttac aattcaaaac ctaacatatt    3600
atattccctc aaagcaggtt cacgatcaca cctgtaccta aaaaaaacat gaagaatata    3660
ttactccatt attatgagat gaaccacttg gcaagagtgg taagctatat aaaaaaatga    3720
```

```
acattattac gagatgttat atgccattat attgattcga agatatatgt ttctttctcc    3780
cacgggcacc taacggatac atgataaggc caaggcagat cacgggaaat tattcgaata    3840
catgttacgc cctattgccg aaaaaaaat gcagggcagg tgttggccgt agcgatttaa    3900
gcacttaagc tggaggttgc cacacttgga tgcaagcgtc tgacccttct aaaaaatcgg    3960
cggctttgtc cgtatccgta tccctatcc aacatctagc tggccacacg acggggctgg    4020
gcagatcgtg gatgccgggt cgacgtcgat cgtcagccat catagaccaa tcgaccatct    4080
gttatggatg cttgctagct agactagtca gacataaaat ttggatactt tctcccaact    4140
gggagacggg gactgatgtg cagctgcacg tgagctaaat ttttccctat aaatatgcat    4200
gaaatactgc attatcttgc cacagccact gccacagcca gataacaagt gcagctggta    4260
gcacgcaacg catagctctg gacttgtagc taggtagcca accggatcca cacgacacca    4320
tgctcgacac caacaaggtg tacgagatca gcaaccacgc caacggcctc tacgccgcca    4380
cctacctctc cctcgacgac tccggcgtgt ccctcatgaa caagaacgac gacgacatcg    4440
acgactacaa cctcaagtgg ttcctcttcc cgatcgacga cgaccagtac atcatcacct    4500
cctacgccgc caacaactgc aaggtgtgga acgtgaacaa cgacaagatt aatgtgtcaa    4560
cctactcctc caccaactcc atccagaagt ggcagatcaa ggccaacggc tcctcctacg    4620
tgatccagtc cgacaacggc aaggtgctca ccgccggcac cggccaggcc ctcggcctca    4680
tccgcctcac cgacgagtcc tccaacaacc cgaaccagca atggaacctg acgtccgtgc    4740
agaccatcca gctcccgcag aagccgatca tcgacaccaa gctcaaggac tacccgaagt    4800
actccccgac cggcaacatc gacaacggca cctcccccgca gctcatgggc tggaccctcg    4860
tgccgtgcat catggtgaac gacccgaaca tcgacaagaa cacccagatc aagaccaccc    4920
cgtactacat cctcaagaag taccagtact ggcagagggc cgtgggctcc aacgtcgcgc    4980
tccgcccgca cgagaagaag tcctacacct acgagtgggg caccgagatc gaccagaaga    5040
ccaccatcat caacaccctc ggcttccaga tcaacatcga cagcggcatg aagttcgaca    5100
tcccggaggt gggcggcggt accgacgaga tcaagaccca gctcaacgag gagctcaaga    5160
tcgagtattc acatgagacg aagatcatgg agaagtacca ggagcagtcc gagatcgaca    5220
acccgaccga ccagtccatg aactccatcg gcttcctcac catcacctcc ctggagctct    5280
accgctacaa cggctccgag atccgcatca tgcagatcca gacctccgac aacgacacct    5340
acaacgtgac ctcctacccg aaccaccagc aggccctgct gctgctgacc aaccactcct    5400
acgaggaggt ggaggagatc accaacatcc cgaagtccac cctcaagaag ctcaagaagt    5460
actacttctg agtcatgagt catgagtcag ttaacctaga cttgtccatc ttctggattg    5520
gccaacttaa ttaatgtatg aaataaaagg atgcacacat agtgacatgc taatcactat    5580
aatgtgggca tcaaagttgt gtgttatgtg taattactag ttatctgaat aaaagagaaa    5640
gagatcatcc atatttctta tcctaaatga atgtcacgtg tctttataat tctttgatga    5700
accagatgca tttcattaac caaatccata tacatataaa tattaatcat atataattaa    5760
tatcaattgg gttagcaaaa caaatctagt ctaggtgtgt tttgcgaatt cccatgcgag    5820
caaagattca aatagaggac ctaacagaac tcgccgtaaa gactggcgaa cagttcatac    5880
agagtctctt acgactcaat gacaagaaga aaatcttcgt caacatggtg agcacgacga    5940
cgcttgtcta ctccaaaaat atcaaagata cagtctcaga agaccaaagg gcaattgaga    6000
cttttcaaca aagggtaata tccggaaacc tcctcggatt ccattgccca gctatctgtc    6060
actttattgt gaagatagtg gaaaggaag gtggctccta caaatgccat cattgcgata    6120
```

| | |
|---|---|
| aaggaaaggc catcgttgaa gatgcctctg ccgacagtgg tcccaaagat ggaccccac | 6180 |
| ccacgaggag catcgtggaa aaagaagacg ttccaaccac gtcttcaaag caagtggatt | 6240 |
| gatgtgatat ctccactgac gtaagggatg acgcacaatc ccactatcct tcgcaagacc | 6300 |
| cttcctctat ataaggaagt tcatttcatt tggagaggac agggtacccg gggatccacc | 6360 |
| atgtctccgg agaggagacc agttgagatt aggccagcta cagcagctga tatggccgcg | 6420 |
| gtttgtgata tcgttaacca ttacattgag acgtctacag tgaactttag gacagagcca | 6480 |
| caaacaccac aagagtggat tgatgatcta gagaggttgc aagatagata cccttggttg | 6540 |
| gttgctgagg ttgagggtgt tgtggctggt attgcttacg ctgggccctg gaaggctagg | 6600 |
| aacgcttacg attggacagt tgagagtact gtttacgtgt cacataggca tcaaaggttg | 6660 |
| ggcctaggat ccacattgta cacacatttg cttaagtcta tggaggcgca aggttttaag | 6720 |
| tctgtggttg ctgttatagg ccttccaaac gatccatctg ttaggttgca tgaggctttg | 6780 |
| ggatacacag cccggggtac attgcgcgca gctggataca agcatggtgg atggcatgat | 6840 |
| gttggttttt ggcaaaggga ttttgagttg ccagctcctc caaggccagt taggccagtt | 6900 |
| acccagatct gagtcgacct gcaggcatgc ccgctgaaat caccagtctc tctctacaaa | 6960 |
| tctatctctc tctataataa tgtgtgagta gttcccagat aagggaatta gggttcttat | 7020 |
| agggtttcgc tcatgtgttg agcatataag aaacccttag tatgtatttg tatttgtaaa | 7080 |
| atacttctat caataaaatt tctaattcct aaaaccaaaa tccagggcga gctcggtacc | 7140 |
| cggggatcct ctagagtcga cctgcaggca tgcccgcgga tatcgatggg ccccggccga | 7200 |
| agcttcggtc cgggccatcg tggcctcttg ctcttcagga tgaagagcta tgtttaaacg | 7260 |
| tgcaagcgct caattcgccc tatagtgagt cgtattacaa tcgtacgcaa ttcagtacat | 7320 |
| taaaaacgtc cgcaatgtgt tattaagttg tctaagcgtc aatttgttta caccacaata | 7380 |
| tatcctgcca | 7390 |

<210> SEQ ID NO 25
<211> LENGTH: 2501
<212> TYPE: DNA
<213> ORGANISM: Artificial Sequence
<220> FEATURE:
<223> OTHER INFORMATION: PCR Amplicon 22I-1

<400> SEQUENCE: 25

| | |
|---|---|
| gcgggacaag ccgttttacg tttggaactg acagaaccgc aacgttgaag gagccactca | 60 |
| gcaagcttac tagtagcgct gtttaaacgc tcttcaactg gaagagcggt tacccggacc | 120 |
| gaagcttgca tgcctgcagt gcagcgtgac ccggtcgtgc ccctctctag ataatgag | 180 |
| cattgcatgt ctaagttata aaaaattacc acatattttt tttgtcacac ttgtttgaag | 240 |
| tgcagtttat ctatctttat acatatattt aaactttact ctacgaataa tataatctat | 300 |
| agtactacaa taatatcagt gttttagaga atcatataaa tgaacagtta gacatggtct | 360 |
| aaaggacaat tgagtatttt gacaacagga ctctacagtt ttatcttttt agtgtgcatg | 420 |
| tgttctcctt ttttttgca aatagcttca cctatataa acttcatcca ttttattagt | 480 |
| acatccattt aggggtttagg gttaatggtt tttatagact aatttttta gtacatctat | 540 |
| tttattctat tttagcctct aaattaagaa aactaaaact ctattttagt tttttattt | 600 |
| aataatttag atataaaata gaataaaata aagtgactaa aaattaaaca atacccttt | 660 |
| aagaaattaa aaaactaag gaaacatttt tcttgtttcg agtagataat gccagcctgt | 720 |
| taaacgccgt cgacgagtct aacggacacc aaccagcgaa ccagcagcgt cgcgtcgggc | 780 |

```
caagcgaagc agacggcacg gcatctctgt cgctgcctct ggacccctct cgagagttcc    840
gctccaccgt tggacttgct ccgctgtcgg catccagaaa ttgcgtggcg gagcggcaga    900
cgtgagccgg cacggcaggc ggcctcctcc tcctctcacg gcaccggcag ctacggggga    960
ttcctttccc accgctcctt cgctttccct tcctcgcccg ccgtaataaa tagacacccc   1020
ctccacaccc tctttcccca acctcgtgtt gttcggagcg cacacacaca caaccagatc   1080
tcccccaaat ccaccgtcg gcacctccgc ttcaaggtac gccgctcgtc ctcccccccc    1140
ccccctctct accttctcta gatcggcgtt ccggtccatg gttagggccc ggtagttcta   1200
cttctgttca tgtttgtgtt agatccgtgt ttgtgttaga tccgtgctgc tagcgttcgt   1260
acacggatgc gacctgtacg tcagacacgt tctgattgct aacttgccag tgtttctctt   1320
tggggaatcc tgggatggct ctagccgttc cgcagacggg atcgatttca tgattttttt   1380
tgtttcgttg catagggttt ggtttgccct tttcctttat ttcaatatat gccgtgcact   1440
tgtttgtcgg gtcatctttt catgctttt tttgtcttgg ttgtgatgat gtggtctggt   1500
tgggcggtcg ttctagatcg gagtagaatt ctgtttcaaa ctacctggtg gatttattaa   1560
ttttggatct gtatgtgtgt gccatacata ttcatagtta cgaattgaag atgatggatg   1620
gaaatatcga tctaggatag gtatacatgt tgatgcgggt tttactgatg catatacaga   1680
gatgcttttt gttcgcttgg ttgtgatgat gtggtgtggt tgggcggtcg ttcattcgtt   1740
ctagatcgga gtagaatact gtttcaaact acctggtgta tttattaatt ttggaactgt   1800
atgtgtgtgt catacatctt catagttacg agtttaagat ggatggaaat atcgatgtag   1860
gataggtata catgttgatg tgggttttac tgatgcatat acatgatggc atatgcagca   1920
tctattcata tgctctaacc ttgagtacct atctattata ataaacaagt atgttttata   1980
attatttga tcttgatata cttggatgat ggcatatgca gcagctatat gtggattttt    2040
ttagccctgc cttcatacgc tatttatttg cttggtactg tttcttttgt cgatgctcac   2100
cctgttgttt ggtgttactt ctgcaggtcg actctagagg atccacacga caccatgtcc   2160
gcccgcgagg tgcacatcga cgtgaacaac aagaccggcc acaccctcca gctggaggac   2220
aagaccaagc tcgacggcgg caggtggcgc acctccccga ccaacgtggc caacgaccag   2280
atcaagacct tcgtggccga atccaacggc ttcatgaccg gcaccgaggg caccatctac   2340
tactcaatta atggcgaggc cgagatcagc ctctacttcg acaacccgtt cgccggctcc   2400
aacaaatacg acggccactc caacaagtcc cagtacgaga tcatcaccca gggcggctcc   2460
ggcaaccagt cccacgtgac ctacaccatc cagaccacct c                       2501
```

<210> SEQ ID NO 26
<211> LENGTH: 3027
<212> TYPE: DNA
<213> ORGANISM: Artificial Sequence
<220> FEATURE:
<223> OTHER INFORMATION: PCR Amplicon 22I-2.

<400> SEQUENCE: 26

```
aacaacaaga ccggccacac cctccagctg gaggacaaga ccaagctcga cggcggcagg     60
tggcgcacct ccccgaccaa cgtggccaac gaccagatca agaccttcgt ggccgaatcc    120
aacggcttca tgaccggcac cgagggcacc atctactact caattaatgg cgaggccgag    180
atcagcctct acttcgacaa cccgttcgcc ggctccaaca atacgacgg ccactccaac    240
aagtcccagt acgagatcat cacccagggc ggctccggca accagtccca cgtgacctac    300
accatccaga ccacctcctc ccgctacggc cacaagtcct gagtcatgag tcatgagtca    360
```

```
gttaacctag acttgtccat cttctggatt ggccaactta attaatgtat gaaataaaag    420
gatgcacaca tagtgacatg ctaatcacta taatgtgggc atcaaagttg tgtgttatgt    480
gtaattacta gttatctgaa taaaagagaa agagatcatc catatttctt atcctaaatg    540
aatgtcacgt gtctttataa ttctttgatg aaccagatgc atttcattaa ccaaatccat    600
atacatataa atattaatca tatataatta atatcaattg ggttagcaaa acaaatctag    660
tctaggtgtg ttttgcgaat gcggccgcgg accgaattgg ggatctgcat gaaagaaact    720
gtcgcactgc tgaaccgcac cttgtcactt tcatcgaaca cgacctgtgc caagatgac     780 ggtgctgcgg tctaagtgag gctgaattgc cttggacaga agcggactcc ctacaattag    840
ttaggccaaa cggtgcatcc atgtgtagct ccgggctcgg gctgtatcgc catctgcaat    900
agcatccatg gagctcgttc catgtagttg gagatgaacc aatgatcggg cgtgtggacg    960
tatgttcctg tgtactccga tagtagagta cgtgttagct ctttcatggt gcaagtgaaa    1020
tttgtgttgg tttaattacc cctacgttag ttgcgggaca ggagacacat catgaattta    1080
aaggcgatga tgtcctctcc tgtaatgtta ttcttttgat gtgatgaatc aaaatgtcat    1140
ataaaacatt tgttgctctt tagttaggcc tgatcgtaga acgaaatgct cgtgtagcgg    1200
ggctacgagc ctatgacgca ataacactgg tttgccggcc cggagtcgct tgacaaaaaa    1260
aagcatgtta agtttattta caattcaaaa cctaacatat tatattccct caaagcaggt    1320
tcacgatcac acctgtacct aaaaaaaaca tgaagaatat attactccat tattatgaga    1380
tgaaccactt ggcaagagtg gtaagctata taaaaaaatg aacattatta cgagatgtta    1440
tatgccatta tattgattcg aagatatatg tttctttctc ccacgggcac ctaacggata    1500
catgataagg ccaaggcaga tcacgggaaa ttattcgaat acatgttacg ccctattgcc    1560
ggaaaaaaaa tgcagggcag gtgttggccg tagcgattta agcacttaag ctggaggttg    1620
ccacacttgg atgcaagcgt ctgacccttc taaaacatcg gcggctttgt ccgtatccgt    1680
atcccctatc cgacatctag ctggccacac gacggggctg gcagatcgt ggatgccggg     1740 tcgacgtcga tcgtcagcca tcatagacca atcgaccatc tgttatggat gcttgctagc    1800
tagactagtc agacataaaa tttggatact ttctcccaac tgggagacgg ggactgatgt    1860
gcagctgcac gtgagctaaa ttttcccta taaatatgca tgaaatactg cattatcttg    1920
ccacagccac tgccacagcc agataacaag tgcagctggt agcacgcaac gcatagctct    1980
ggacttgtag ctaggtagcc aaccggatcc acacgacacc atgctcgaca ccaacaaggt    2040
gtacgagatc agcaaccacg ccaacggcct ctacgccgcc acctacctct ccctcgacga    2100
ctccggcgtg tccctcatga acaagaacga cgacgacatc gacgactaca acctcaagtg    2160
gttcctcttc ccgatcgacg acgaccagta catcatcacc tcctacgccg ccaacaactg    2220
caaggtgtgg aacgtgaaca cgacaagat taatgtgtca acctactcct ccaccaactc    2280
catccagaag tggcagatca aggccaacgg ctcctcctac gtgatccagt ccgacaacgg    2340
caaggtgctc accgccggca ccggccaggc cctcggcctc atccgcctca ccgacgagtc    2400
ctccaacaac ccgaaccagc aatggaacct gacgtccgtg cagaccatcc agctcccgca    2460
gaagccgatc atcgacacca agctcaagga ctacccgaag tactccccga ccggcaacat    2520
cgacaacggc acctccccgc agctcatggg ctggaccctc gtgccgtgca tcatggtgaa    2580
cgacccgaac atcgacaaga cacccagat caagaccacc ccgtactaca tcctcaagaa    2640
gtaccagtac tggcagaggg ccgtgggctc aacgtcgcg ctccgccgc acgagaagaa      2700 gtcctacacc tacgagtggg gcaccgagat cgaccagaag accaccatca tcaacaccct    2760
```
cggcttccag atcaacatcg acagcggcat gaagttcgac atcccggagg tgggcggcgg    2820
taccgacgag atcaagaccc agctcaacga ggagctcaag atcgagtatt cacatgagac    2880
gaagatcatg gagaagtacc aggagcagtc cgagatcgac aacccgaccg accagtccat    2940
gaactccatc ggcttcctca ccatcacctc cctggagctc taccgctaca acggctccga    3000
gatccgcatc atgcagatcc agacctc                                        3027

<210> SEQ ID NO 27
<211> LENGTH: 2830
<212> TYPE: DNA
<213> ORGANISM: Artificial Sequence
<220> FEATURE:
<223> OTHER INFORMATION: PCR Amplicon 22I-3.

<400> SEQUENCE: 27
tacaacctca gtggttcct cttcccgatc gacgacgacc agtacatcat cacctcctac       60
gccgccaaca actgcaaggt gtggaacgtg aacaacgaca agattaatgt gtcaacctac     120
tcctccacca actccatcca gaagtggcag atcaaggcca acggctcctc ctacgtgatc     180
cagtccgaca acggcaaggt gctcaccgcc ggcaccggcc aggccctcgg cctcatccgc     240
ctcaccgacg agtcctccaa caacccgaac cagcaatgga acctgacgtc cgtgcagacc     300
atccagctcc cgcagaagcc gatcatcgac accaagctca aggactaccc gaagtactcc     360
ccgaccggca acatcgacaa cggcacctcc ccgcagctca tgggctggac cctcgtgccg     420
tgcatcatgg tgaacgaccc gaacatcgac aagaacaccc agatcaagac caccccgtac     480
tacatcctca agaagtacca gtactggcag agggccgtgg gctccaacgt cgcgctccgc     540
ccgcacgaga agaagtccta cacctacgag tggggcaccg agatcgacca agaagaccacc     600 atcatcaaca ccctcggctt ccagatcaac atcgacagcg gcatgaagtt cgacatcccg     660
gaggtgggcg gcggtaccga cgagatcaag acccagctca cgaggagct caagatcgag     720 tattcacatg agacgaagat catggagaag taccaggagc agtccgagat cgacaacccg     780
accgaccagt ccatgaactc catcggcttc ctcaccatca cctccctgga gctctaccgc     840
tacaacggct ccgagatccg catcatgcag atccagacct ccgacaacga cacctacaac     900
gtgacctcct acccgaacca ccagcaggcc ctgctgctgc tgaccaacca ctcctacgag     960
gaggtggagg agatcaccaa catcccgaag tccaccctca gaagctcaa gaagtactac    1020 ttctgagtca tgagtcatga gtcagttaac ctagacttgt ccatcttctg gattggccaa    1080
cttaattaat gtatgaaata aaaggatgca cacatagtga catgctaatc actataatgt    1140
gggcatcaaa gttgtgtgtt atgtgtaatt actagttatc tgaataaaag agaaagagat    1200
catccatatt tcttatccta aatgaatgtc acgtgtcttt ataattcttt gatgaaccag    1260
atgcatttca ttaaccaaat ccatatacat ataaatatta atcatatata attaatatca    1320
attgggttag caaaacaaat ctagtctagg tgtgttttgc gaattcccat ggagtcaaag    1380
attcaaatag aggacctaac agaactcgcc gtaaagactg gcgaacagtt catacagagt    1440
ctcttacgac tcaatgacaa gaagaaaatc ttcgtcaaca tggtggagca cgacacgctt    1500
gtctactcca aaaatatcaa agatacagtc tcagaagacc aaagggcaat tgagactttt    1560
caacaaaggg taatatccgg aaacctcctc ggattccatt gcccagctat ctgtcacttt    1620
attgtgaaga tagtggaaaa ggaaggtggc tcctacaaat gccatcattg cgataaagga    1680
aaggccatcg ttgaagatgc ctctgccgac agtggtccca agatggaccc ccacccacg    1740 aggagcatcg tggaaaaaga gacgttccaa ccacgtcttt caaagcaagt ggattgatgt    1800

-continued

```
gatatctcca ctgacgtaag ggatgacgca caatcccact atccttcgca agacccttcc    1860
tctatataag gaagttcatt tcatttggag aggacagggt acccggggat ccaccatgtc    1920
tccggagagg agaccagttg agattaggcc agctacagca gctgatatgg ccgcggtttg    1980
tgatatcgtt aaccattaca ttgagacgtc tacagtgaac tttaggacag agccacaaac    2040
accacaagag tggattgatg atctagagag gttgcaagat agataccctt ggttggttgc    2100
tgaggttgag ggtgttgtgg ctggtattgc ttacgctggg ccctggaagg ctaggaacgc    2160
ttacgattgg acagttgaga gtactgttta cgtgtcacat aggcatcaaa ggttgggcct    2220
aggatccaca ttgtacacac atttgcttaa gtctatggag gcgcaaggtt ttaagtctgt    2280
ggttgctgtt ataggccttc caaacgatcc atctgttagg ttgcatgagg ctttgggata    2340
cacagcccgg ggtacattgc gcgcagctgg atacaagcat ggtggatggc atgatgttgg    2400
tttttggcaa agggattttg agttgccagc tcctccaagg ccagttaggc cagttaccca    2460
gatctgagtc gacctgcagg catgcccgct gaaatcacca gtctctctct acaaatctat    2520
ctctctctat aataatgtgt gagtagttcc cagataaggg aattagggtt cttatagggt    2580
ttcgctcatg tgttgagcat ataagaaacc cttagtatgt attgtatttg taaaatact    2640 tctatcaata aaatttctaa ttcctaaaac caaaatccag ggcgagctcg gtacccgggg    2700
atcctctaga gtcgacctgc aggcatgccc gcggatatcg atgggcccg gccgaagctt    2760 cggtccgggc catcgtggcc tcttgctctt caggatgaag agctatgttt aaacgtgcaa    2820
gcgctcaatt                                                          2830
```

<210> SEQ ID NO 28
<211> LENGTH: 136
<212> TYPE: DNA
<213> ORGANISM: Artificial Sequence
<220> FEATURE:
<223> OTHER INFORMATION: PCR Amplicon O784/O564

<400> SEQUENCE: 28

```
aatccacaag attggagcaa acgaccaaaa attcacaagg attggcggct gacattgcca     60
gcgcgggatc gcatgcggcg gcggcggccg gggcgagcac gggagcaggc gacagtcgag    120
ctccattgga acgtag                                                   136
```

<210> SEQ ID NO 29
<211> LENGTH: 263
<212> TYPE: DNA
<213> ORGANISM: Artificial Sequence
<220> FEATURE:
<223> OTHER INFORMATION: PCR Amplicon O784/O543

<400> SEQUENCE: 29

```
aatccacaag attggagcaa acgaccaaaa attcacaagg attggcggct gacattgcca     60
gcgcgggatc gcatgcggcg gcggcggccg gggcgagcac gggagcaggc gacagtcgag    120
ctccattgga acgtagaaat acttaagggc aaggtctcca aatacttgaa aaataggaa     180 aaagaagaaa atacatgaaa tgatattgaa atcaattgga agatgttatg aatcttgttt    240
ttgcaaagcg aacgattcag atg                                           263
```

<210> SEQ ID NO 30
<211> LENGTH: 227
<212> TYPE: DNA
<213> ORGANISM: Artificial Sequence
<220> FEATURE:
<223> OTHER INFORMATION: PCR Amplicon O569/O577

<400> SEQUENCE: 30

```
ggtcaagtgg acacttggtc actcatttaa tccctccctc tcctctttta tccctctttt      60
tggtgtattc accaatagtg gtgtgcacct gtgattggct cgtaaaaatt cttggacgga     120
tggaagagtg aagagataag caagtcaaag aaaagtaaca acgaagcttc atcagctaca     180
aattttggcc caactggttg caccagcacc aaacttacgt atacatg                   227
```

<210> SEQ ID NO 31
<211> LENGTH: 492
<212> TYPE: DNA
<213> ORGANISM: Artificial Sequence
<220> FEATURE:
<223> OTHER INFORMATION: PCR Amplicon 0570/0542

<400> SEQUENCE: 31

```
gagtgaagag ataagcaagt caagaaaag taacaacgaa gcttcatcag ctacaaattt       60
tggcccaact ggttgcacca gccaaaact tacgtataca tgattatctc tgtttccctc      120
atttcgaaga aaaaacggg tttcaaaacc cactgctttc aggagtaaaa aagataata      180
atctgaaaca ttgcttccac cttggccctt atttggttac gttgcaattc accccaatcc    240
acatgtggat tgagatggat tgcagtgtag ctagacaaac ccttaggccc tgtttgcata    300
ggaatacacc aggaattatt ccagctaatc aaaatttata taaatgagag aaacaattcg    360
gataggaatt gttccaggac ttcattctgc agtaaccgaa cggcccctta atccacccca    420
atacacgtgg attggagtgg attgaggtac agccaaacaa ggcctaagtg cagatcaaat    480
aaatcacccg tc                                                         492
```

<210> SEQ ID NO 32
<211> LENGTH: 555
<212> TYPE: DNA
<213> ORGANISM: Artificial Sequence
<220> FEATURE:
<223> OTHER INFORMATION: PCR Amplicon 0784/0215

<400> SEQUENCE: 32

```
aatccacaag attggagcaa acgaccaaaa attcacaagg attggcggct gacattgcca      60
gcgcgggatc gcatgcggcg gcggcggccg gggcgagcac gggagcaggc gacagtcgag     120
ctccattgga acgtagaaat acttaagggc aaggtctcca aatacttgaa aaataggaa     180
aaagaagaaa atacatgaaa tgatattgaa atcaattgga agatgttatg aatcttgttt    240
ttgcaaagcg aacgattcag atggcaaaac tatgaatctt tttgtttgaa gtcccaaata    300
taaaattttc tcgtactcac caacattggt gcgcacctgt gattggctca taaaaattct    360
tggagggacg gaagaaagag tgaagggata agcaagtaaa agcgctcaaa cactgatagt    420
ttaaactgaa ggcgggaaac gacaatctga tcatgagcgg agaattaagg gagtcacgtt    480
atgacccctg ccgatgacgc gggacaagcc gttttacgtt tggaactgac agaaccgcaa    540
cgttgaagga gccac                                                     555
```

<210> SEQ ID NO 33
<211> LENGTH: 547
<212> TYPE: DNA
<213> ORGANISM: Artificial Sequence
<220> FEATURE:
<223> OTHER INFORMATION: PCR Amplicon 0219/0577

<400> SEQUENCE: 33

```
cgtgcaagcg ctcaattcgc cctatagtga gtcgtattac aatcgtacgc aattcagtac      60
```

| | | |
|---|---|---|
| attaaaaacg tccgcaatgt gttattaagt tgtctaagcg tcaattttt ccttctatgg | 120 |
| tcccgtttgt ttatcctcta aattatataa tccagcttaa ataagttaag agacaaacaa | 180 |
| acaacacaga ttattaaata gattatgtaa tctagatacc tagattatgt aatccataag | 240 |
| tagaatatca ggtgcttata taatctatga gctcgattat ataatcttaa aagaaaacaa | 300 |
| acagagcccc tataaaaagg ggtcaagtgg acacttggtc actcatttaa tccctccctc | 360 |
| tcctcttta tccctctttt tggtgtattc accaatagtg gtgtgcacct gtgattggct | 420 |
| cgtaaaaatt cttggacgga tggaagagtg aagagataag caagtcaaag aaaagtaaca | 480 |
| acgaagcttc atcagctaca aattttggcc caactggttg caccagcacc aaacttacgt | 540 |
| atacatg | 547 |

<210> SEQ ID NO 34
<211> LENGTH: 243
<212> TYPE: DNA
<213> ORGANISM: Artificial Sequence
<220> FEATURE:
<223> OTHER INFORMATION: PCR Amplicon 0506/0476

<400> SEQUENCE: 34

| | | |
|---|---|---|
| tctcgtactc accaacattg gtgcgcacct gtgattggct cataaaaatt cttggaggga | 60 |
| cggaagaaag agtgaaggga taagcaagta aaagcgctca acactgata gtttaaactg | 120 |
| aaggcgggaa acgacaatct gatcatgagc ggagaattaa gggagtcacg ttatgacccc | 180 |
| cgccgatgac gcgggacaag ccgttttacg tttggaactg acagaaccgc aacgttgaag | 240 |
| gag | 243 |

<210> SEQ ID NO 35
<211> LENGTH: 754
<212> TYPE: DNA
<213> ORGANISM: Artificial Sequence
<220> FEATURE:
<223> OTHER INFORMATION: PCR Amplicon 0447/0577

<400> SEQUENCE: 35

| | | |
|---|---|---|
| aacccttagt atgtatttgt atttgtaaaa tacttctatc aataaaattt ctaattccta | 60 |
| aaaccaaaat ccagggcgag ctcggtaccc ggggatcctc tagagtcgac ctgcaggcat | 120 |
| gcccgcggat atcgatgggc cccggccgaa gcttcggtcc gggccatcgt ggcctcttgc | 180 |
| tcttcaggat gaagagctat gtttaaacgt gcaagcgctc aattcgccct atagtgagtc | 240 |
| gtattacaat cgtacgcaat tcagtacatt aaaaacgtcc gcaatgtgtt attaagttgt | 300 |
| ctaagcgtca attttttccct tctatggtcc cgtttgttta tcctctaaat tatataatcc | 360 |
| agcttaaata agttaagaga caaacaaaca acacagatta ttaaatagat tatgtaatct | 420 |
| agatacctag attatgtaat ccataagtag aatatcaggt gcttatataa tctatgagct | 480 |
| cgattatata atcttaaaag aaaacaaaca gagcccctat aaaagggggt caagtggaca | 540 |
| cttggtcact catttaatcc ctcctctcc tcttttatcc ctcttttttgg tgtattcacc | 600 |
| aatagtggtg tgcacctgtg attggctcgt aaaaattctt ggacggatgg aagagtgaag | 660 |
| agataagcaa gtcaaagaaa agtaacaacg aagcttcatc agctacaaat tttggcccaa | 720 |
| ctggttgcac cagcaccaaa cttacgtata catg | 754 |

<210> SEQ ID NO 36
<211> LENGTH: 25
<212> TYPE: DNA
<213> ORGANISM: Artificial Sequence
<220> FEATURE:

```
<223> OTHER INFORMATION: Oligonucleotide primer

<400> SEQUENCE: 36
cgtattacaa tcgtacgcaa ttcag                                          25

<210> SEQ ID NO 37
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 37
ggataaacaa acgggaccat agaag                                          25

<210> SEQ ID NO 38
<211> LENGTH: 104
<212> TYPE: DNA
<213> ORGANISM: Artificial Sequence
<220> FEATURE:
<223> OTHER INFORMATION: Amplicon of SEQ ID NOs: 36 and 37

<400> SEQUENCE: 38
cgtattacaa tcgtacgcaa ttcagtacat taaaaacgtc cgcaatgtgt tattaagttg    60
tctaagcgtc aatttttccc ttctatggtc ccgtttgttt atcc                    104

<210> SEQ ID NO 39
<211> LENGTH: 25
<212> TYPE: DNA
<213> ORGANISM: Artificial Sequence
<220> FEATURE:
<223> OTHER INFORMATION: IVR1 (0197)  Primer used to generate a 226 bp
      amplicon as an internal positive control

<400> SEQUENCE: 39
ccgctgtatc acaagggctg gtacc                                          25

<210> SEQ ID NO 40
<211> LENGTH: 25
<212> TYPE: DNA
<213> ORGANISM: Artificial Sequence
<220> FEATURE:
<223> OTHER INFORMATION: IVR2 (0198) Primer used to generate a 226 bp
      amplicon as an internal positive control

<400> SEQUENCE: 40
ggagcccgtg tagagcatga cgatc                                          25
```

CORN EVENT DAS-59122-7 AND METHODS FOR DETECTION THEREOF

CROSS-REFERENCE TO RELATED APPLICATIONS

This application is a divisional of U.S. Ser. No. 11/938,483, filed Nov. 12, 2007, which is a divisional of U.S. Ser. No. 11/237,222 filed Sep. 28, 2005, now U.S. Pat. No. 7,323,556, which claims the benefit of U.S. Provisional Application Ser. No. 60/614,225, filed Sep. 29, 2004, the contents of all of which are herein incorporated by reference in their entirety.

FIELD OF INVENTION

Embodiments of the present invention relate to the field of plant molecular biology, specifically an embodiment of the invention relates to a DNA construct for conferring insect resistance to a plant. Embodiments of the invention more specifically relate to an insect resistant corn plant DAS-59122-7 and to assays for detecting the presence of corn plant DAS-59122-7 DNA in a sample and compositions thereof.

BACKGROUND OF INVENTION

An embodiment of this invention relates to the insect resistant corn (*Zea mays*) plant DAS-59122-7, also referred to as maize line DAS-59122-7 or maize event DAS-59122-7, and to the DNA plant expression construct of corn plant DAS-59122-7 and the detection of the transgene/flanking insertion region in corn plant DAS-59122-7 and progeny thereof.

Corn is an important crop and is a primary food source in many areas of the world. Damage caused by insect pests is a major factor in the loss of the world's corn crops, despite the use of protective measures such as chemical pesticides. In view of this, insect resistance has been genetically engineered into crops such as corn in order to control insect damage and to reduce the need for traditional chemical pesticides. One group of genes which have been utilized for the production of transgenic insect resistant crops are the delta-endotoxins from *Bacillus thuringiensis* (B.t). Delta-endotoxins have been successfully expressed in crop plants such as cotton, potatoes, rice, sunflower, as well as corn, and have proven to provide excellent control over insect pests. (Perlak, F. J et al. (1990) *Bio/Technology* 8, 939-943; Perlak, F. J. et al. (1993) *Plant Mol. Biol.* 22: 313-321; Fujimoto H. et al. (1993) *Bio/Technology* 11: 1151-1155; Tu et al. (2000) *Nature Biotechnology* 18:1101-1104; PCT publication number WO 01/13731; and Bing J W et al. (2000) Efficacy of Cry1F Transgenic Maize, 14th Biennial International Plant Resistance to Insects Workshop, Fort Collins, Colo.).

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising et al., *Ann. Rev. Genet* 22:421-477, 1988). At the same time the presence of the transgene at different locations in the genome will influence the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example, or for use in environmental monitoring, monitoring traits in crops in the field, or monitoring products derived from a crop harvest, as well as for use in ensuring compliance of parties subject to regulatory or contractual terms.

It is possible to detect the presence of a transgene by any nucleic acid detection method known in the art including, but not limited to, the polymerase chain reaction (PCR) or DNA hybridization using nucleic acid probes. These detection methods generally focus on frequently used genetic elements, such as promoters, terminators, marker genes, etc., because for many DNA constructs, the coding region is interchangeable. As a result, such methods may not be useful for discriminating between different events, particularly those produced using the same DNA construct or very similar constructs unless the DNA sequence of the flanking DNA adjacent to the inserted heterologous DNA is known. For example, an event-specific PCR assay is described in U.S. Pat. No. 6,395,485 for the detection of elite event GAT-ZM1. Accordingly, it would be desirable to have a simple and discriminative method for the identification of event DAS-59122-7.

SUMMARY OF INVENTION

Embodiments of this invention relate to methods for producing and selecting an insect resistant monocot crop plant. More specifically, a DNA construct is provided that when expressed in plant cells and plants confers resistance to insects. According to one aspect of the invention, a DNA construct, capable of introduction into and replication in a host cell, is provided that when expressed in plant cells and plants confers insect resistance to the plant cells and plants. The DNA construct is comprised of a DNA molecule named PHI17662A and it includes three (3) transgene expression cassettes. The first expression cassette comprises a DNA molecule which includes the promoter, 5' untranslated exon, and first intron of the maize ubiquitin (Ubi-1) gene (Christensen et al. (1992) *Plant Mol. Biol.* 18:675-689 and Christensen and Quail (1996) *Transgenic Res.* 5:213-218) operably connected to a DNA molecule encoding a B.t. δ-endotoxin identified as Cry34Ab1 (U.S. Pat. Nos. 6,127,180, 6,624,145 and 6,340,593) operably connected to a DNA molecule comprising a Pin II transcriptional terminator isolated from potato (Gyheung An et al. (1989) *Plant Cell.* 1:115-122). The second transgene expression cassette of the DNA construct comprises a DNA molecule encoding the wheat peroxidase promoter (Hertig et al. (1991) *Plant Mol. Biol.* 16:171-174) operably connected to a DNA molecule encoding a B.t. δ-endotoxin identified as Cry35Ab1 (U.S. Pat. Nos. 6,083,499, 6,548,291 and 6,340,593) operably connected to a DNA molecule comprising a Pin II transcriptional terminator isolated from potato (Gyheung An et al. (1989) *Plant Cell.* 1:115-122). The third transgene expression cassette of the DNA construct comprises a DNA molecule of the cauliflower mosaic virus (CaMV) 35S promoter (Odell J. T. et al. (1985) *Nature* 313: 810-812; Mitsuhara et al. (1996) *Plant Cell Physiol.* 37: 49-59) operably connected to a DNA molecule encoding a phosphinothricin acetyltransferase (PAT) gene (Wohlleben W. et al. (1988) *Gene* 70: 25-37) operably connected to a DNA molecule comprising a 3' transcriptional terminator from (CaMV) 35S (see Mitsuhara et al. (1996) *Plant Cell Physiol.* 37: 49-59). Plants containing the DNA construct are also provided.

According to another embodiment of the invention, compositions and methods are provided for identifying a novel corn plant designated DAS-59122-7, which methods are based on primers or probes which specifically recognize the 5' and/or 3' flanking sequence of DAS-59122-7. DNA molecules are provided that comprise primer sequences that when utilized in a PCR reaction will produce amplicons unique to the transgenic event DAS-59122-7. These molecules may be selected from the group consisting of:

```
                                         (SEQ ID NO: 1)
5'-GTGGCTCCTTCAACGTTGCGGTTCTGTC-3';

(SEQ ID NO: 2)
5'-CGTGCAAGCGCTCAATTCGCCCTATAGTG-3';

(SEQ ID NO: 3)
5'-AATTGAGCGCTTGCACGTTT-3';

(SEQ ID NO: 4)
5'-AACAACAAGACCGGCCACACCCTC-3';

(SEQ ID NO: 5)
5'-GAGGTGGTCTGGATGGTGTAGGTCA-3';

(SEQ ID NO: 6)
5'-TACAACCTCAAGTGGTTCCTCTTCCCGA-3';

(SEQ ID NO: 7)
5'-GAGGTCTGGATCTGCATGATGCGGA-3';

(SEQ ID NO: 8)
5'-AACCCTTAGTATGTATTTGTATT-3';

(SEQ ID NO: 9)
5'-CTCCTTCAACGTTGCGGTTCTGTCAG-3';

(SEQ ID NO: 10)
5'-TTTTGCAAAGCGAACGATTCAGATG-3';

(SEQ ID NO: 11)
5'-GCGGGACAAGCCGTTTTACGTTT-3';

(SEQ ID NO: 12)
5'-GACGGGTGATTTATTTGATCTGCAC-3';

(SEQ ID NO: 13)
5'-CATCTGAATCGTTCGCTTTGCAAAA-3';

(SEQ ID NO: 14)
5'-CTACGTTCCAATGGAGCTCGACTGTC-3';

(SEQ ID NO: 15)
5'-GGTCAAGTGGACACTTGGTCACTCA-3';

(SEQ ID NO: 16)
5'-GAGTGAAGAGATAAGCAAGTCAAAG-3';

(SEQ ID NO: 17)
5'-CATGTATACGTAAGTTTGGTGCTGG-3';

(SEQ ID NO: 18)
5'-AATCCACAAGATTGGAGCAAACGAC-3'

(SEQ ID NO: 36)
5'-CGTATTACAATCGTACGCAATTCAG-3';

(SEQ ID NO: 37)
5'-GGATAAACAAACGGGACCATAGAAG-3'
``` and complements thereof. The corn plant and seed comprising these molecules is an embodiment of this invention. Further, kits utilizing these primer sequences for the identification of the DAS-59122-7 event are provided.

An additional embodiment of the invention relates to the specific flanking sequences of DAS-59122-7 described herein, which can be used to develop specific identification methods for DAS-59122-7 in biological samples. More particularly, the invention relates to the 5' and/or 3' flanking regions of DAS-59122-7, SEQ ID NO: 19, 5' flanking and SEQ ID NO: 20, 3' flanking, respectively, which can be used for the development of specific primers and probes. A further embodiment of the invention relates to identification methods for the presence of DAS-59122-7 in biological samples based on the use of such specific primers or probes.

According to another embodiment of the invention, methods of detecting the presence of DNA corresponding to the corn event DAS-59122-7 in a sample are provided. Such methods comprise: (a) contacting the sample comprising DNA with a DNA primer set, that when used in a nucleic acid amplification reaction with genomic DNA extracted from corn event DAS-59122-7 produces an amplicon that is diagnostic for corn event DAS-59122-7; (b) performing a nucleic acid amplification reaction, thereby producing the amplicon; and (c) detecting the amplicon.

DNA molecules that comprise the novel transgene/flanking insertion region, SEQ ID NO: 21, 5' flanking plus 1000 internal and SEQ ID NO: 22, 3' flanking plus 1000 internal and are homologous or complementary to SEQ ID NO: 21 and SEQ ID NO: 22 are an embodiment of this invention.

DNA sequences that comprise the novel transgene/flanking insertion region, SEQ ID NO: 21 are an embodiment of this invention. DNA sequences that comprise a sufficient length of polynucleotides of transgene insert sequence and a sufficient length of polynucleotides of maize genomic and/or flanking sequence from maize plant DAS-59122-7 of SEQ ID NO: 21 that are useful as primer sequences for the production of an amplicon product diagnostic for maize plant DAS-59122-7 are included.

In addition, DNA sequences that comprise the novel transgene/flanking insertion region, SEQ ID NO: 22 are provided. DNA sequences that comprise a sufficient length of polynucleotides of transgene insert sequence and a sufficient length of polynucleotides of maize genomic and/or flanking sequence from maize plant DAS-59122-7 of SEQ ID NO: 22 that are useful as primer sequences for the production of an amplicon product diagnostic for maize plant DAS-59122-7 are included.

According to another embodiment of the invention, the DNA sequences that comprise at least 11 or more nucleotides of the transgene portion of the DNA sequence of SEQ ID NO: 21 or complements thereof, and a similar length of 5' flanking maize DNA sequence of SEQ ID NO: 21 or complements thereof are useful as DNA primers in DNA amplification methods. The amplicons produced using these primers are diagnostic for maize event DAS-59122-7. Therefore, embodiments of the invention also include the amplicons produced by DNA primers homologous or complementary to SEQ ID NO: 21.

According to another embodiment of the invention, the DNA sequences that comprise at least 11 or more nucleotides of the transgene portion of the DNA sequence of SEQ ID NO: 22 or complements thereof, and a similar length of 3' flanking maize DNA sequence of SEQ ID NO: 22 or complements thereof are useful as DNA primers in DNA amplification methods. The amplicons produced using these primers are diagnostic for maize event DAS-59122-7. Therefore, embodiments of the invention also include the amplicons produced by DNA primers homologous or complementary to SEQ ID NO: 22.

More specifically, a pair of DNA molecules comprising a DNA primer set, wherein the DNA molecules are identified as SEQ ID NO: 18 or complements thereof and SEQ ID NO: 1 or complements thereof; SEQ ID NO: 2 or complements thereof and SEQ ID NO: 17 or complements thereof; SEQ ID NO: 10 or complements thereof and SEQ ID NO: 9 or complements thereof; SEQ ID NO: 8 or complements thereof and SEQ ID NO: 17 or complements thereof; and SEQ ID NO: 36 or complements thereof and SEQ ID NO: 37 or complements thereof are embodiments of the invention.

Further embodiments of the invention include the amplicon comprising the DNA molecules of SEQ ID NO: 18 and SEQ ID NO: 1; the amplicon comprising the DNA molecules of SEQ ID NO: 2 and SEQ ID NO: 17; the amplicon comprising the DNA molecules of SEQ ID NO: 10 and SEQ ID NO: 9; the amplicon comprising the DNA molecules of SEQ ID NO: S and SEQ ID NO: 17; and the amplicon comprising the DNA molecules of SEQ ID NO: 36 and SEQ ID NO: 37.

Further embodiments of the invention include the following primers, which are useful in detecting or characterizing event DAS-59122-7: SEQ ID NO: 11 or complements thereof; SEQ ID NO: 5 or complements thereof; SEQ ID NO: 4 or complements thereof; SEQ ID NO: 7 or complements thereof; SEQ ID NO: 6 or complements thereof; SEQ ID NO: 3 or complements thereof; SEQ ID NO: 18 or complements thereof; SEQ ID NO: 14 or complements thereof; SEQ ID NO: 13 or complements thereof; SEQ ID NO: 15 or complements thereof; SEQ ID NO: 17 or complements thereof; SEQ ID NO: 16 or complements thereof; and SEQ ID NO: 12 or complements thereof. Further embodiments also include the amplicons produced by pairing any of the primers listed above.

According to another embodiment of the invention, methods of detecting the presence of a DNA molecule corresponding to the DAS-59122-7 event in a sample, such methods comprising: (a) contacting the sample comprising DNA extracted from a corn plant with a DNA probe, molecule that hybridizes under stringent hybridization conditions with DNA extracted from corn event DAS-59122-7 and does not hybridize under the stringent hybridization conditions with a control corn plant DNA; (b) subjecting the sample and probe to stringent hybridization conditions; and (c) detecting hybridization of the probe to the DNA. More specifically, a method for detecting the presence of a DNA molecule corresponding to the DAS-59122-7 event in a sample, such methods, consisting of (a) contacting the sample comprising DNA extracted from a corn plant with a DNA probe molecule that consists of sequences that are unique to the event, e.g. junction sequences, wherein said DNA probe molecule hybridizes under stringent hybridization conditions with DNA extracted from corn event DAS-59122-7 and does not hybridize under the stringent hybridization conditions with a control corn plant DNA; (b) subjecting the sample and probe to stringent hybridization conditions; and (c) detecting hybridization of the probe to the DNA.

In addition, a kit and methods for identifying event DAS-59122-7 in a biological sample which detects a DAS-59122-7 specific region within SEQ ID NO: 23 are provided.

DNA molecules are provided that comprise at least one junction sequence of DAS-59122-7 selected from the group consisting of SEQ ID NO: 32, 33, 34, and 35 and complements thereof; wherein a junction sequence spans the junction between heterologous DNA inserted into the genome and the DNA from the corn cell flanking the insertion site, i.e. flanking DNA, and is diagnostic for the DAS-59122-7 event.

According to another embodiment of the invention, methods of producing an insect resistant corn plant that comprise the steps of: (a) sexually crossing a first parental corn line comprising the expression cassettes of the invention, which confers resistance to insects, and a second parental corn line that lacks insect resistance, thereby producing a plurality of progeny plants; and (b) selecting a progeny plant that is insect resistant. Such methods may optionally comprise the further step of back-crossing the progeny plant to the second parental corn line to producing a true-breeding corn plant that is insect resistant.

A further embodiment of the invention provides a method of producing a corn plant that is resistant to insects comprising transforming a corn cell with the DNA construct PHI17662A (SEQ ID NO: 24), growing the transformed corn cell into a corn plant, selecting the corn plant that shows resistance to insects, and further growing the corn plant into a fertile corn plant. The fertile corn plant can be self pollinated or crossed with compatible corn varieties to produce insect resistant progeny.

Another embodiment of the invention further relates to a DNA detection kit for identifying maize event DAS-59122-7 in biological samples. The kit comprises a first primer which specifically recognizes the 5' or 3' flanking region of DAS-59122-7, and a second primer which specifically recognizes a sequence within the foreign. DNA of DAS-59122-7, or within the flanking DNA, for use in a PCR identification protocol. A further embodiment of the invention relates to a kit for identifying event DAS-59122-7 in biological samples, which kit comprises a specific probe having a sequence which corresponds or is complementary to, a sequence having between 80% and 100% sequence identity with a specific region of event DAS-59122-7. The sequence of the probe corresponds to a specific region comprising part of the 5' or 3' flanking region of event DAS-59122-7.

The methods and kits encompassed by the embodiments of the present invention can be used for different purposes such as, but not limited to the following: to identify event DAS-59122-7 in plants, plant material or in products such as, but not limited to, food or feed products (fresh or processed) comprising, or derived from plant material; additionally or alternatively, the methods and kits can be used to identify transgenic plant material for purposes of segregation between transgenic and non-transgenic material; additionally or alternatively, the methods and kits can be used to determine the quality of plant material comprising maize event DAS-59122-7. The kits may also contain the reagents and materials necessary for the performance of the detection method.

A further embodiment of this invention relates to the DAS-59122-7 corn plant or its parts, including, but not limited to, pollen, ovules, vegetative cells, the nuclei of pollen cells, and the nuclei of egg cells of the corn plant DAS-59122-7 and the progeny derived thereof. The corn plant and seed DAS- 59122-7 from which the DNA primer molecules provide a specific amplicon product is an embodiment of the invention.

The foregoing and other aspects of the invention will become more apparent from the following detailed description and accompanying drawing.

BRIEF DESCRIPTION OF THE DRAWINGS

FIG. 1. DNA sequence (SEQ ID NO: 23) showing the transgenic insert PHI17662A, as well as the sequences flanking the transgenic insert. The 5' and 3' border regions, by 1 to bp2593 and bp 9937 to bp 11922, respectively, are underlined. Two nucleotide differences (bp 6526 and bp 6562) based on comparison to the transforming plasmid PHP17662 are noted in bold and underlined.

FIG. 2. Schematic diagram of the B.t. Cry34/35Ab1 event DAS-59122-7 insert region is divided into three separate sections; the 5' border region with corn genomic DNA, the intact T-DNA insert, and the 3' border region with corn genomic DNA. The two arrows beneath the diagram of the insert indicate the start and end points of the sequence derived from 5' and 3' genome walking fragments. Other boxes beneath the diagram of the insert represent PCR fragments that were amplified from genomic DNA of event DAS-59122-7 and sequenced to cover the intact T-DNA insert and the 5' and 3' insert/border junction regions.

DETAILED DESCRIPTION

Figure 3:
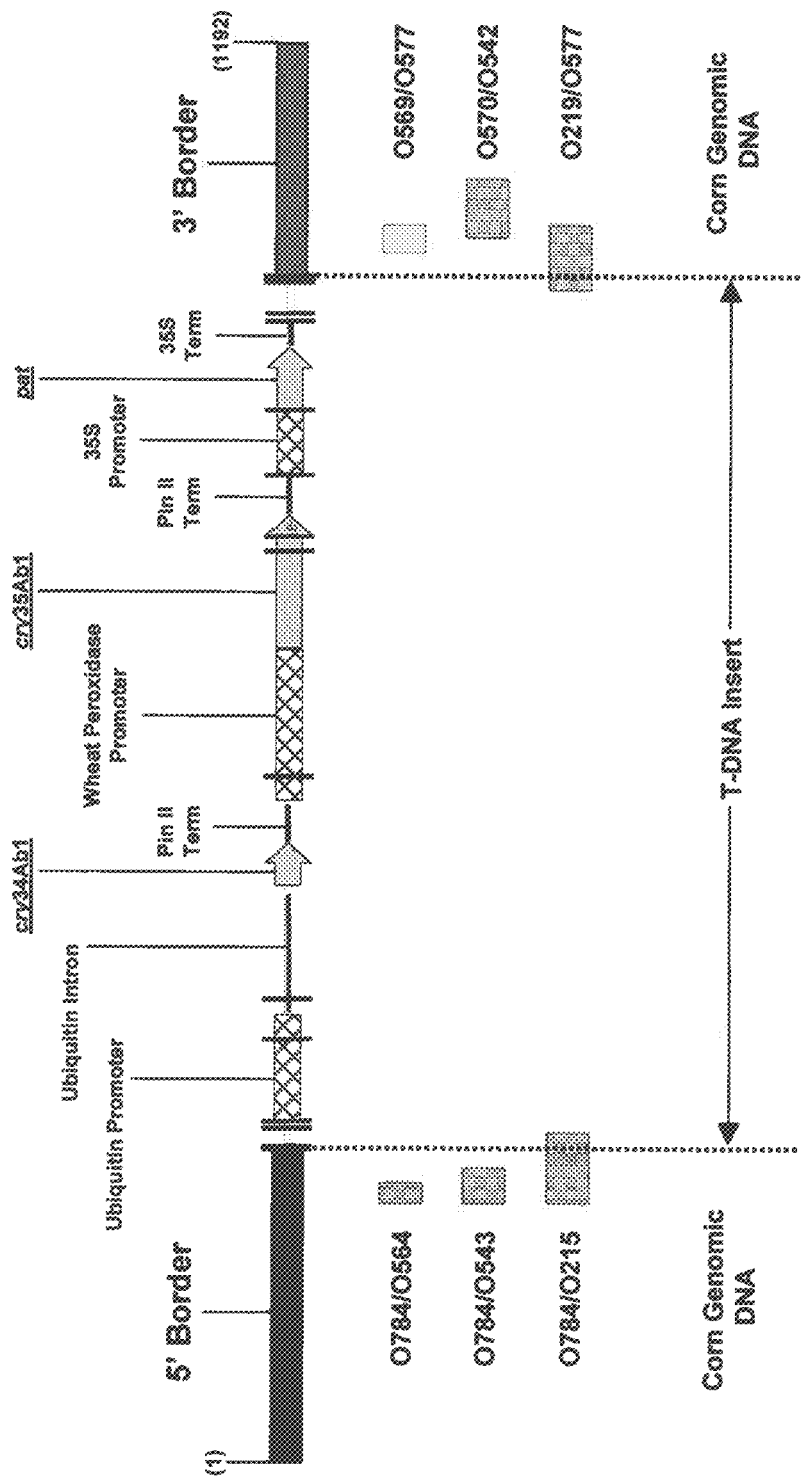
FIG. 3. Schematic diagram of the B.t. Cry34/35Ab1 event DAS-59122-7 insert region is divided into three separate sections; the 5' border region with corn genomic DNA, the intact T-DNA insert, and the 3' border region with corn genomic DNA. Boxes beneath the diagram of the insert represent PCR fragments located in either the genomic border regions or across the 5' and 3' junction regions of the T-DNA insert with corn genomic DNA that were amplified from genomic DNA from event DAS-59122-7.

The following definitions and methods are provided to better define the present invention and to guide those of ordinary skill in the art in the practice of the present invention. Unless otherwise noted, terms are to be understood according to conventional usage by those of ordinary skill in the relevant art Definitions of common terms in molecular biology may also be found in Rieger et al. *Glossary of Genetics: Classical and Molecular*, 5th edition, Springer-Verlag; New York, 1991; and Lewin, *Genes V*, Oxford University Press: New York, 1994. The nomenclature for DNA bases as set forth at 37 CFR §1.822 is used.

As used herein, the term "comprising" means "including but not limited to".

As used herein, the term "corn" means *Zea mays* or maize and includes all plant varieties that can be bred with corn, including wild maize species.

As used herein, the term "DAS-59122-7 specific" refers to a nucleotide sequence which is suitable for discriminatively identifying event DAS-59122-7 in plants, plant material, or in products such as, but not limited to, food or feed products (fresh or processed) comprising, or derived from plant material.

As used herein, the terms "insect resistant" and "impacting insect pests" refers to effecting changes in insect feeding, growth, and/or behavior at any stage of development, including but not limited to: killing the insect; retarding growth; preventing reproductive capability; inhibiting feeding; and the like.

As used herein, the terms "pesticidal activity" and "insecticidal activity" are used synonymously to refer to activity of an organism or a substance (such as, for example, a protein) that can be measured by numerous parameters including, but not limited to, pest mortality, pest weight loss, pest attraction, pest repellency, and other behavioral and physical changes of a pest after feeding on and/or exposure to the organism or substance for an appropriate length of time. For example "pesticidal proteins" are proteins that display pesticidal activity by themselves or in combination with other proteins.

"Coding sequence" refers to a nucleotide sequence that codes for a specific amino acid sequence. As used herein, the terms "encoding" or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. "Foreign" refers to material not normally found in the location of interest. Thus "foreign DNA" may comprise both recombinant DNA as well as newly introduced, rearranged DNA of the plant. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. The site in the plant genome where a recombinant DNA has been inserted may be referred to as the "insertion site" or "target site".

As used herein, "insert DNA" refers to the heterologous DNA within the expression cassettes used to transform the plant material while "flanking DNA" can exist of either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least twenty (20) base pair, preferably at least fifty (50) base pair, and up to five thousand (5000) base pair which is located either immediately upstream of and contiguous with or immediately downstream of and contiguous with the original foreign insert DNA molecule. Transformation procedures leading to random integration of the foreign DNA will result in transformants containing different flanking regions characteristic and unique for each transformant. When recombinant DNA is introduced into a plant through traditional crossing, its flanking regions will generally not be changed. Transformants will also contain unique junctions between a piece of heterologous insert DNA and genomic DNA, or two (2) pieces of genomic DNA, or two (2) pieces of heterologous DNA. A "junction" is a point where two (2) specific DNA fragments join. For example, a junction exists where insert DNA joins flanking DNA. A junction point also exists in a transformed organism where two (2) DNA fragments join together in a manner that is modified from that found in the native organism. "Junction DNA" refers to DNA that comprises a junction point.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency. Examples of translation leader sequences have been described (Turner and Foster (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

A "protein" or "polypeptide" is a chain of amino acids arranged in a specific order determined by the coding sequence in a polynucleotide encoding the polypeptide.

A DNA construct is an assembly of DNA molecules linked together that provide one or more expression cassettes. The DNA construct may be a plasmid that is enabled for self replication in a bacterial cell and contains various endonuclease enzyme restriction sites that are useful for introducing DNA molecules that provide functional genetic elements, i.e., promoters, introns, leaders, coding sequences, 3' termination regions, among others; or a DNA construct may be a linear assembly of DNA molecules, such as an expression cassette. The expression cassette contained within a DNA construct comprise the necessary genetic elements to provide transcription of a messenger RNA. The expression cassette can be designed to express in prokaryote cells or eukaryotic cells. Expression cassettes of the embodiments of the present invention are designed to express in plant cells.

The DNA molecules of embodiments of the invention are provided in expression cassettes for expression in an organism of interest. The cassette will include 5' and 3' regulatory sequences operably linked to a coding sequence. "Operably linked" means that the nucleic acid sequences being linked are contiguous and, where necessary to join two protein coding regions, contiguous and in the same reading frame. Operably linked is intended to indicate a functional linkage between a promoter and a second sequence, wherein the promoter sequence initiates and mediates transcription of the DNA sequence corresponding to the second sequence. The cassette may additionally contain at least one additional gene to be cotransformed into the organism. Alternatively, the additional gene(s) can be provided on multiple expression cassettes or multiple DNA constructs.

The expression cassette will include in the 5' to 3' direction of transcription: a transcriptional and translational initiation region, a coding region, and a transcriptional and translational termination region functional in the organism serving as a host. The transcriptional initiation region (i.e., the promoter) may be native or analogous, or foreign or heterologous to the host organism. Additionally, the promoter may be the natural sequence or alternatively a synthetic sequence. The expression cassettes may additionally contain 5' leader sequences in the expression cassette construct. Such leader sequences can act to enhance translation.

It is to be understood that as used herein the term "transgenic" includes any cell, cell line, callus, tissue, plant part, or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

An insect resistant DAS-59122-7 corn plant can be bred by first sexually crossing a first parental corn plant consisting of a corn plant grown from the transgenic DAS-59122-7 corn plant and progeny thereof derived from transformation with the expression cassettes of the embodiments of the present invention that confers insect resistance, and a second parental corn plant that lacks insect resistance, thereby producing a plurality of first progeny plants; and then selecting a first progeny plant that is resistant to insects; and selfing the first progeny plant, thereby producing a plurality of second progeny plants; and then selecting from the second progeny plants an insect resistant plant. These steps can further include the back-crossing of the first insect resistant progeny plant or the second insect resistant progeny plant to the second parental corn plant or a third parental corn plant, thereby producing a corn plant that is resistant to insects.

As used herein, the term "plant" includes reference to whole plants, plant organs (e.g., leaves, stems, roots, etc.), seeds, plant cells, and progeny of same. Parts of transgenic plants understood to be within the scope of the invention comprise, for example, plant cells, protoplasts, tissues, callus, embryos as well as flowers, stems, fruits, leaves, and roots originating in transgenic plants or their progeny previously transformed with a DNA molecule of the invention and therefore consisting at least in part of transgenic cells, are also an embodiment of the present invention.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70-73; U.S. Pat. No. 4,945,050, incorporated herein by reference). Additional transformation methods are disclosed below.

Thus, isolated polynucleotides of the invention can be incorporated into recombinant constructs, typically DNA constructs, which are capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., (1985; Supp. 1987) *Cloning Vectors: A Laboratory Manual*, Weissbach and Weissbach (1989) *Methods for Plant Molecular Biology*, (Academic Press, New York); and Flevin et al., (1990) *Plant Molecular Biology Manual*, (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

It is also to be understood that two different transgenic plants can also be mated to produce offspring that contain two independently segregating added, exogenous genes. Selling of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcos J. ed., American Society of Agronomy, Madison Wis. (1987).

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of isolated DNA from corn event DAS-59122-7 whether from a corn plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the invention refer to their use for amplification of a target nucleic acid sequence, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference).

Probes and primers are of sufficient nucleotide length to bind to the target DNA sequence specifically in the hybridization conditions or reaction conditions determined by the operator. This length may be of any length that is of sufficient length to be useful in a detection method of choice. Generally, eleven (11) nucleotides or more in length, eighteen (18) nucleotides or more, and twenty-two (22) nucleotides or more, are used. Such probes and primers hybridize specifically to a target sequence under high stringency hybridization conditions. Probes and primers according to embodiments of the present invention may have complete DNA sequence similarity of contiguous nucleotides with the target sequence, although probes differing from the target DNA sequence and that retain the ability to hybridize to target DNA sequences may be designed by conventional methods. Probes can be used as primers, but are generally designed to bind to the target DNA or RNA and are not used in an amplification process.

Specific primers can be used to amplify an integration fragment to produce an amplicon that can be used as a "specific probe" for identifying event DAS-59122-7 in biological samples. When the probe is hybridized with the nucleic acids of a biological sample under conditions which allow for the binding of the probe to the sample, this binding can be detected and thus allow for an indication of the presence of event DAS-59122-7 in the biological sample. Such identification of a bound probe has been described in the art. In an embodiment of the invention the specific probe is a sequence which, under optimized conditions, hybridizes specifically to a region within the 5' or 3' flanking region of the event and also comprises a part of the foreign DNA contiguous therewith. The specific probe may comprise a sequence of at least 80%, between 80 and 85%, between 85 and 90%, between 90 and 95%, and between 95 and 100% identical (or complementary) to a specific region of the event.

Methods for preparing and using probes and primers are described, for example, in *Molecular Cloning: A Laboratory Manual*, $2^{nd}$ ed, vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, Wis.); and Primer (Version 0.5©, 1991, Whitehead Institute for Biomedical Research, Cambridge, Mass.). Additionally, the sequence can be visually scanned and primers manually identified using guidelines known to one of skill in the art.

A "kit" as used herein refers to a set of reagents for the purpose of performing the method embodiments of the invention, more particularly, the identification of the event DAS-59122-7 in biological samples. The kit of the invention can be used, and its components can be specifically adjusted, for purposes of quality control (e.g. purity of seed lots), detection of event DAS-59122-7 in plant material, or material comprising or derived from plant material, such as but not limited to food or feed products. "Plant material" as used herein refers to material which is obtained or derived from a plant.

Primers and probes based on the flanking DNA and insert sequences disclosed herein can be used to confirm (and, if necessary, to correct) the disclosed sequences by conventional methods, e.g., by re-cloning and sequencing such sequences. The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, a Practical Approach*, IRL Press, Washington, D.C. (1985), departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

In hybridization reactions, specificity is typically the function of post-hybridization washes, the critical factors being the ionic strength and temperature of the final wash solution. The thermal melting point (Tm) is the temperature (under defined ionic strength and pH) at which 50% of a complementary target sequence hybridizes to a perfectly matched probe. For DNA-DNA hybrids, the Tm can be approximated from the equation of Meinkoth and Wahl (1984) *Anal. Biochem.* 138:267-284: Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the Tm for the specific sequence and its complement at a defined ionic strength and pH. However, severely stringent conditions can utilize a hybridization and/or wash at 1, 2, 3, or 4° C. lower than the Tm; moderately stringent conditions can utilize a hybridization and/or wash at 6, 7, 8, 9, or 10° C. lower than the Tm; low stringency conditions can utilize a hybridization and/or wash at 11, 12, 13, 14, 15, or 20° C. lower than the Tm.

Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecu-* lar Cloning: A Laboratory Manual (2d ed., Cold Spring Harbor Laboratory Press, Plainview, N.Y.).

As used herein, a substantially homologous sequence is a nucleic acid molecule that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in Current Protocols in Molecular Biology, John Wiley & Sons, N.Y. (1989), 6.3.1-6.3.6. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of a destabilizing agent such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. A nucleic acid of the invention may specifically hybridize to one or more of the nucleic acid molecules unique to the DAS-59122-7 event or complements thereof or fragments of either under moderately stringent conditions.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS 4:11-17; the local homology algorithm of Smith et al. (1981) Adv. Appl. Math. 2:482; the homology alignment algorithm of Needleman and Wunsch (1970) J. Mol. Biol. 48:443-453; the search-for-similarity-method of Pearson and Lipman (1988) Proc. Natl. Acad. Sci. 85:2444-2448; the algorithm of Karlin and Altschul (1990) Proc. Natl. Acad. Sci. USA 87:2264, modified as in Karlin and Altschul (1993) Proc. Natl. Acad. Sci. USA 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (version 3.0, copyright 1997); and GAP, BESTFIT, BLAST, FASTA, and TFASTA in the Wisconsin Genetics Software Package, Version 10 (available from Accelrys, 9685 Scranton Road, San Diego, Calif. 92121, USA). Alignments using these programs can be performed using the default parameters.

The CLUSTAL program is well described by Higgins and Sharp, Gene 73: 237-244 (1988); Higgins and Sharp, CABIOS 5: 151-153 (1989); Corpet, et al., Nucleic Acids Research 16: 10881-90 (1988); Huang, et al., Computer Applications in the Biosciences 8: 155-65 (1992), and Pearson, et al., Methods in Molecular Biology 24: 307-331 (1994). The ALIGN and the ALIGN PLUS programs are based on the algorithm of Myers and Miller (1988) supra. The BLAST programs of Altschul et al. (1990) J. Mol. Biol. 215:403 are based on the algorithm of Karlin and Altschul (1990) supra. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995). Alignment may also be performed manually by visual inspection.

To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.hlm.nih.gov.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic acid amplification of a target nucleic acid sequence that is part of a nucleic acid template. For example, to determine whether a corn plant resulting from a sexual cross contains transgenic event genomic DNA from the corn plant of the invention, DNA extracted from the corn plant tissue sample may be subjected to a nucleic acid amplification method using a DNA primer pair that includes a first primer derived from flanking sequence adjacent to the insertion site of inserted heterologous DNA, and a second primer derived from the inserted heterologous DNA to produce an amplicon that is diagnostic for the presence of the event DNA. Alternatively, the second primer may be derived from the flanking sequence. The amplicon is of a length and has a sequence that is also diagnostic for the event. The amplicon may range in length from the combined length of the primer pairs plus one nucleotide base pair to any length of amplicon producible by a DNA amplification protocol. Alternatively, primer pairs can be derived from flanking sequence on both sides of the inserted DNA so as to produce an amplicon that includes the entire insert nucleotide sequence of the PHI17662A expression construct as well as the sequence flanking the transgenic insert, see FIG. 1 (SEQ ID NO: 23), approximately twelve (12) Kb in size. A member of a primer pair derived from the flanking sequence may be located a distance from the inserted DNA sequence, this distance can range from one nucleotide base pair up to the limits of the amplification reaction, or about twenty thousand nucleotide base pairs. The use of the term "amplicon" specifically excludes primer dimers that may be formed in the DNA thermal amplification reaction.

Nucleic acid amplification can be accomplished by any of the various nucleic acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al. Academic press, San Diego, 1990. PCR amplification methods have been developed to amplify up to 22 Kb of genomic DNA and up to 42 Kb of bacteriophage DNA (Cheng et al. *Proc. Natl. Acad. Sci. USA* 91:5695-5699, 1994). These methods as well as other methods known in the art of DNA amplification may be used in the practice of the embodiments of the present invention. It is understood that a number of parameters in a specific PCR protocol may need to be adjusted to specific laboratory conditions and may be slightly modified and yet allow for the collection of similar results. These adjustments will be apparent to a person skilled in the art.

The amplicon produced by these methods may be detected by a plurality of techniques, including, but not limited to, Genetic Bit Analysis (Nikiforov, et al. *Nucleic Acid Res.* 22:4167-4175, 1994) where a DNA oligonucleotide is designed which overlaps both the adjacent flanking DNA sequence and the inserted DNA sequence. The oligonucleotide is immobilized in wells of a microwell plate. Following PCR of the region of interest (using one primer in the inserted sequence and one in the adjacent flanking sequence) a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the Pyrosequencing technique as described by Winge (*Innov. Pharma. Tech.* 00: 18-24, 2000). In this method an oligonucleotide is designed that overlaps the adjacent DNA and insert DNA junction. The oligonucleotide is hybridized to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen et al., (*Genome Res.* 9:492-498, 1999) is also a method that can be used to detect an amplicon of the invention. Using this method an oligonucleotide is designed which overlaps the flanking and inserted DNA junction. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi et al. (*Nature Biotech.* 14:303-308, 1996). Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction.

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Applicants made a deposit of at least 2500 seeds of hybrid corn (maize) seed comprising event DAS-59122-7 on Oct. 4, 2010 with the American Type Culture Collection (ATCC), Manassas, Va. 20110 USA. The deposit was assigned ATCC Patent Deposit Designation PTA-11384. Access to this deposit will be available during the pendency of the application to the Commissioner of Patents and Trademarks and persons determined by the Commissioner to be entitled thereto upon request. Upon the grant of a patent from the present application, Applicants will make the deposit available to the public pursuant to 37 C.F.R. §1.808. This deposit of hybrid corn (maize) seed comprising event DAS-59122-7 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§1.801-1.809, including providing an indication of the viability of the sample upon deposit. Applicant has no authority to waive any restrictions imposed by law on the transfer of biological material or its transportation in commerce. Applicant does not waive any infringement of their rights granted under this patent or under the Plant Variety Protection Act (7 U.S.C. §2321 et seq.).

The disclosure of each reference set forth herein is incorporated herein by reference in its entirety.

EXAMPLES

Example 1

Transformation of Maize by *Agrobacterium* Transformation and Regeneration of Transgenic Plants Containing the Cry34Ab1 and Cry35Ab1 (Cry34/35Ab1) Genes A DNA molecule of approximately 7.4 Kb, designated PHI17662A (SEQ ID NO: 24), which includes a first transgene expression cassette comprising a DNA molecule which includes the promoter, 5' untranslated exon, and first intron of the maize ubiquitin (Ubi-1) gene (Christensen et al. (1992) *Plant Mol. Biol.* 18:675-689 and Christensen and Quail (1996) *Transgenic Res.* 5:213-218) operably connected to a DNA molecule encoding a B.t. δ-endotoxin identified as Cry34Ab1 (U.S. Pat. Nos. 6,127,180, 6,624,145 and 6,340,593) operably connected to a DNA molecule comprising a Pin II transcriptional terminator isolated from potato (Gyheung An et al. (1989) *Plant Cell.* 1:115-122). The second transgene expression cassette of the DNA construct comprises a DNA molecule encoding the wheat peroxidase promoter (Hertig et al. (1991) *Plant Mol. Biol.* 16:171-174) operably connected to a DNA molecule encoding a B.t. δ-endotoxin identified as Cry35Ab1 (U.S. Pat. Nos. 6,083,499, 6,548,291 and 6,340,593) operably connected to a DNA molecule comprising a Pin II transcriptional terminator isolated from potato (Gyheung An et al. (1989) *Plant Cell.* 1:115-122). The third transgene expression cassette of the DNA construct comprises a DNA molecule of the cauliflower mosaic virus (CaMV) 35S promoter (Odell J. T. et al. (1985) *Nature* 313: 810-812; Mitsuhara et al. (1996) *Plant Cell Physiol.* 37: 49-59) operably connected to a DNA molecule encoding a phosphinothricin acetyltransferase (PAT) gene (Wohlleben W. et al. (1988) *Gene* 70: 25-37) operably connected to a DNA molecule comprising a 3' transcriptional terminator from (CaMV) 35S (see Mitsuhara et al. (1996) *Plant Cell Physiol.* 37: 49-59) was used to transform maize embryo tissue.

B.t. Cry34/35 Ab1 maize plants were obtained by *Agrobacterium* transformation, the method of Zhao was employed (U.S. Pat. No. 5,981,840, and PCT patent publication WO98/32326; the contents of which are hereby incorporated by reference). Briefly, immature embryos were isolated from maize and the embryos contacted with a suspension of *Agrobacterium*, where the bacteria was capable of transferring PHI17662 DNA (SEQ ID NO:24) to at least one cell of at least one of the immature embryos (step 1: the infection step). Specifically, in this step the immature embryos were immersed in an *Agrobacterium* suspension for the initiation of inoculation. The embryos were co-cultured for a time with the *Agrobacterium* (step 2: the co-cultivation step). Specifically, the immature embryos were cultured on solid medium following the infection step. Following this co-cultivation period a "resting" step was provided. In this resting step, the embryos were incubated in the presence of at least one antibiotic known to inhibit the growth of *Agrobacterium* without the addition of a selective agent for plant transformants (step 3: resting step). In particular, the immature embryos are cultured on solid medium with antibiotic, but without a selecting agent, for elimination of *Agrobacterium* and for a resting phase for the infected cells. Next, inoculated embryos were cultured on medium containing a selective agent and growing transformed callus was recovered (step 4: the selection step). Specifically, the immature embryos were cultured on solid medium with a selective agent resulting in the selective growth of transformed cells. The callus was then regenerated into plants (step 5: the regeneration step), and, specifically, calli grown on selective medium were cultured on solid medium to regenerate the plants. Individual embryos were kept physically separate during culture, and the majority of explants died on the selective medium.

Those embryos that survived and produced healthy, glufosinate-resistant callus tissue were assigned unique identification codes representing putative transformation events, and continually transferred to fresh selection medium. Plants were regenerated from tissue derived from each unique event and transferred to the greenhouse. Leaf samples were taken for molecular analysis to verify the presence of the transgene by PCR and to confirm expression of the Cry34/35Ab1 protein by ELISA. Plants were then subjected to a whole plant bioassay using western corn rootworm insects. Positive plants were crossed with inbred lines to obtain seed from the initial transformed plants. A number of lines were evaluated in the field. The DAS-59122-7 event was selected from a population of independent transgenic events based on a superior combination of characteristics, including insect resistance and agronomic performance.

Example 2

Identification of *Bacillus thuringiensis* Cry34/35Ab1 Maize Line DAS-59122-7

Seed from event DAS-59122-7 was evaluated. The T1S2 seed represents transformation into the Hi-II background, followed by a cross with inbred line PH09B and two rounds of self-crossing. All seed were obtained from Pioneer Hi-Bred (Johnston, Iowa). Primary characterization was conducted on plant leaf tissue during the study by confirmation of phosphinothricin acetyltransferase (PAT) activity via herbicide leaf painting and Cry34Ab1 expression using lateral flow devices.

Control substances in this study were defined as unmodified seed representative of the test substance background. Control seeds of Hi-II and PH09B backgrounds were used as negative controls. These unmodified seed do not contain the plant transcription units for the cry34Ab1, cry35Ab1, and pat genes. All seed were obtained from Pioneer Hi-Bred (Johnston, Iowa).

DNA samples from two additional B.t. Cry34/35Ab1 events, event DAS-45214-4 and event DAS-45216-6, were used as negative controls for event specific PCR analysis. The two events were produced through *Agrobacterium* transformation using the same vector used to produce event DAS-59122-7 and therefore contained the plant transcription units for the cry34Ab1, cry35Ab1, and pat genes. However, the insertions sites of the T-DNA in events DAS-45214-4 and DAS-45216-6, including genomic DNA border regions, were different from that in event DAS-59122-7. DNA samples from event DAS-45214-4 and event DAS-45216-6 were isolated and characterized by Southern blot analysis. (Data not shown.)

Corn seed for event DAS-59122-7 and unmodified control seed (Hi-II and PH09B) were planted in growth chambers at the DuPont Experimental Station (Wilmington, Del.) to produce sufficient numbers of plants for DNA analysis. For characterization of event DAS-59122-7, ten (10) T1S2 seeds were planted. Ten (10) seeds were also planted for each unmodified control line. One (1) seed was planted per pot, and the pot was uniquely identified. Planting and growing conditions were conducive to healthy plant growth including regulated light and water.

Leaf samples were collected for each of the control and event DAS-59122-7 plants. For each sample, sufficient leaf material from above the growing point was collected and placed in a pre-labeled sample bag. The samples were placed on dry ice and were transferred to an ultralow freezer following collection. All samples were maintained frozen until processing. All leaf samples were uniquely labeled with the plant identifier and the date of harvest.

To confirm the expression of the Cry34Ab1 protein in event DAS-59122-7 and the absence of expression in the controls, leaf samples were collected from all event DAS-59122-7 and control plants, and screened for transgenic protein using lateral flow devices specific for Cry34Ab1 (Strategic Diagnostics, Inc., Newark, Del.). Leaf punches were taken from each plant and ground in a phosphate buffered saline solution with Tween 20 to crudely extract the protein. A strip device was dipped into the extract to determine the presence or absence of the Cry34Ab1 protein. The immunoassay results were used to confirm the identity of the test substance plants prior to molecular analysis as shown in Table 1.

To confirm the expression of phosphinothricin acetyltransferase (PAT) in event DAS-59122-7 plants, herbicide leaf painting was conducted. All plants used in this study were leaf painted to confirm plant identity. Plants were assayed prior to the R1 growth stage. Assays were conducted following a standard procedure known in the art for herbicide leaf painting for the identification of PAT-expressing transgenic plants. Specifically, a portion of one leaf of each plant was treated with approximately 2% solution of glufosinate herbicide, Basta® (Bayer CropScience) in water and visually checked for brown or necrotic tissue in the painted leaf area 4-12 days after application. Results for each plant were recorded and used to determine expression of PAT in each test plant as shown in Table 1. As shown in Table 1, of the ten (10) plants tested for event DAS-59122-7 T1S2 generation, six (6) plants expressed both Cry34Ab1 and PAT, while four (4) plants did not express either protein. All unmodified controls tested negative for both CryAb1 And PAT assays (data not shown).

TABLE 1

Cry34Ab1 and PAT Protein Expression and Southern Hybridization Data for B.t. Cry34/35Ab1 Event DAS-59122-7

| Plant ID | Sample ID | Cry34Ab1 and PAT Expression[1] | Southern Blot cry34Ab1 Probe[2] | Southern Blot cry35Ab1 Probe[2] | Southern Blot pat Probe[2] |
|---|---|---|---|---|---|
| 02-122C 1 | DAS59122-7 T1S2 1 | positive | + | + | + |
| 02-122C 2 | DAS59122-7 T1S2 2 | positive | + | + | + |
| 02-122C 3 | DAS59122-7 T1S2 3 | positive | + | + | + |
| 02-122C 4 | DAS59122-7 T1S2 4 | negative | − | − | − |
| 02-122C 5 | DAS59122-7 T1S2 5 | positive | + | + | + |
| 02-122C 6 | DAS59122-7 T1S2 6 | negative | − | − | − |
| 02-122C 7 | DAS59122-7 T1S2 7 | positive | + | + | + |
| 02-122C 8 | DAS59122-7 T1S2 8 | negative | − | − | − |
| 02-122C 9 | DAS59122-7 T1S2 9 | negative | − | − | − |
| 02-122C 10 | DAS59122-7 T1S2 10 | positive | + | + | + |

[1]Positive Cry34Ab1 expression indicates detection of protein expression as determined by the immunoassay-based lateral flow device specific for Cry34Ab1 protein detection. Negative indicates no detection of the Cry34Ab1 protein. Positive PAT expression indicates plants that were tolerant to the herbicide treatment and negative indicates plants that were sensitive to the herbicide.
[2]+ indicates hybridization signal on Southern blot; − indicates no hybridization signal on Southern blot. The cry34Ab1 gene probe hybridized to the expected internal T-DNA fragment of 1.915 kb, the cry35Ab1 gene probe hybridized to the expected internal T-DNA fragment of 2.607 kb, and the pat gene probe hybridized to a 3.4 kb border fragment consistent with a single intact T-DNA insertion as determined by Southern blot analysis.

Example 3

Southern Blot Analysis of *Bacillus thuringiensis* Cry34/35Ab1 Maize Line DAS-59122-7

One gram quantities of leaf samples were ground under liquid nitrogen, and the genomic DNA was isolated using DNeasy® Plant Mini Kit (Qiagen, Valencia, Calif.) or using a standard Urea Extraction Buffer procedure. Following extraction, the DNA was visualized on an agarose gel to determine the DNA quality, and was quantified using Pico Green® reagent (Molecular Probes, Inc., Eugene, Oreg.) and spectrofluorometric analysis.

The 1 Kb DNA Ladder (Invitrogen, Carlsbad, Calif.) was used to estimate DNA fragment sizes on agarose gels.

Genomic DNA isolated from event DAS-59122-7 plants was digested with Nco I and electrophoretically separated, transferred to nylon membranes, and hybridized to the cry34Ab1, cry35Ab1 and pat gene probes using standard procedures known in the art. Blots were exposed to X-ray film for one or more time periods to detect hybridizing fragments and to visualize molecular weight standards. Images were then digitally captured by photographing X-ray films and/or by detection with a Lumi-Imager™ instrument (Roche, Indianapolis, Ind.). The sizes of detected bands were documented for each probe. Southern blot analysis was used as a means of verifying the presence of the insertion in the test plants and confirming that all plants from event DAS-59122-7 contained the same insertion as shown in Table 1. (Southern blots not shown.) Southern blot analysis indicated that event DAS-59122-7 contained a single insertion consisting of an intact copy of the T-DNA region from plasmid PHP17662, while the null segregants, as determined by the protein expression analysis did not hybridize to the gene probes. Further, event DAS-59122-7 plants expressing the two proteins exhibited identical hybridization patterns on Southern blots (data not shown). Specifically, the cry34Ab1 gene probe hybridized to the expected internal T-DNA fragment of 1.915 kb, the cry35Ab1 gene probe hybridized to the expected internal T-DNA fragment of 2.607 kb, and the pat gene probe hybridized to a 3.4 kb border fragment consistent with a single intact T-DNA insertion as determined by Southern blot results.

Example 4

T-DNA Insert and Flanking Border Region Sequencing of *Bacillus thuringiensis* Cry34/35Ab1 Maize Line DAS-59122-7

The T-DNA insert and flanking border regions were cloned from B.t. Cry34/35Ab1 event DAS59122-7 using PCR based methods as diagramed in FIGS. 2 and 3. Specifically, sequences bordering the 5' and 3' ends of the insert in event DAS-59122-7 were obtained using two genome walking techniques. The first walking method was essentially the method as described for the Universal Genome Walker Kit (BD Biosciences Clontech, Palo Alto, Calif.), and the second method was conducted according to the splinkerette protocol outlined in Devon et al., (1995) *Nucleic Acids Research* 23 (9):1644-1645, with modifications as described by Stover (2001), U. C. Irvine (personal communication).

Briefly, genomic DNA was digested with various restriction enzymes (Dra I, EcoR V, Pvu II, Sma I and Stu I for the Universal Genome Walker method and BamH I, EcoR I, Hind III, and Xba I for the splinkerette method) and then ligated to blunt-end adaptors for the Genome Walker method and to adaptors specific for the restriction enzyme used for the splinkerette method. The adaptors for both genome walking methods were designed to prevent extension of the 3' end of the adaptor during PCR and thus reduce or eliminate nonspecific amplification. The adaptor-ligated genomic DNA fragments were then referred to as genome walker libraries or splinkerette libraries, one library for each restriction enzyme. Libraries were prepared from genomic DNA isolated from three individual T1S2 plants of B.t. Cry34/35Ab1 event DAS-59122-7; plants DAS-59122-7 T1S2 1, DAS-59122-7 T1S2 2 and DAS-59122-7 T1S2 10, and from one Hi-II and one PH09B control plant.

Following construction of the libraries, nested PCR amplifications were completed to amplify the target sequence using Advantage™-GC Genomic PCR kit (BD Biosciences Clontech, Palo Alto, Calif.). The primary PCR amplification used one primer with identity to the adaptor and one gene specific primer. The adaptor primer will not amplify a product in the first cycle of the primary PCR and only products from the gene specific primer will be produced. Annealing and amplification from the adaptor primer only occurs after the complementary strand has been produced from the gene specific primer. Following primary PCR amplification, a secondary nested PCR reaction was performed to increase the specificity of the genomic PCR reactions. The nested primers consisted of gene-specific and adaptor-specific sequences internal to the respective primers used in the primary PCR.

For 5' flanking border sequences, nested PCR was initiated using primers specific to the 5' end of the inserted T-DNA along with primers complementary to the adaptor sequence ligated onto the digested DNA. Similarly, cloning of the 3' flanking border sequence started with a primer specific for the 3' end of the inserted T-DNA and a primer complementary to the adaptor sequence. DNA sequences internal to the T-DNA Right Border and Left Border sequences within the T-DNA region were used as the starting points for "walking out" to the maize genomic sequence, because they represented unique sequence (not homologous to endogenous maize genomic sequences) from which to anchor the genome walking primers.

The products produced by the nested PCR were analyzed by agarose gel electrophoresis (data not shown). Fragments visible in libraries prepared from one or more of the event DAS-59122-7 DNA samples and absent in libraries prepared from the HI-II and PH09B genomic DNA samples were identified for further characterization. The identified PCR amplified fragments were separated by preparatory gel electrophoresis, isolated using a QIAquick Gel Extraction Kit (Qiagen), and sent directly for sequencing or cloned into a pGEM-T Easy plasmid vector using the pGEM-T Easy Vector System I (Promega Corp., Madison, Wis.) prior to DNA sequencing. Sequencing reactions were carried out with primers used for the nested PCR amplification or with primers specific for use with the pGEM-T Easy vector. The sequence obtained was used to design additional gene specific primers to continue "walking out" into the unknown maize genomic sequence. Multiple rounds of genome walking were performed until at least 500 bp of border sequence from the ends of the T-DNA insert were obtained.

To ensure validity of the flanking border sequences, additional event-specific PCR amplifications on genomic DNA from event DAS-59122-7 were performed. The amplified fragments were sequenced in order to further extend the region of sequence overlap from the T-DNA insert region into the 5' and 3' bordering genomic DNA. Primers, shown in Table 2, were designed based on the sequence obtained from the genome walking experiments to amplify a fragment spanning the unique junction of the T-DNA with the corn genomic DNA. Primer set 03-O-506/02-O-476 (SEQ ID NO: 10/SEQ ID NO:9) spanned the 5' junction and amplified a 313 bp fragment (from bp 2427 to bp 2739, see FIG. 1), and primer set 02-O-447/03-O-577 (SEQ ID NO: 8/SEQ ID No:17) spanned the 3' junction and amplified a 754 bp fragment (from bp 9623 to bp 10376, see FIG. 1).

TABLE 2

Primer Sequences

| Primer Name | Sequence (5'-3') | Target Sequence Location (bp to bp)[1] |
|---|---|---|
| 02-O-215 | (SEQ ID NO: 1) GTGGCTCCTTCAACGTTGCGGTTCTGTC | 2743-2716 |
| 02-O-219 | (SEQ ID NO: 2) CGTGCAAGCGCTCAATTCGCCCTATAGTG | 9830-9858 |
| 02-O-227 | (SEQ ID NO: 3) AATTGAGCGCTTGCACGTTT | 9846-9827 |

TABLE 2-continued

Primer Sequences

| Primer Name | Sequence (5'-3') | Target Sequence Location (bp to bp)[1] |
|---|---|---|
| 02-O-370 | (SEQ ID NO: 4) AACAACAAGACCGGCCACACCCTC | 4871-4894 |
| 02-O-371 | (SEQ ID NO: 5) GAGGTGGTCTGGATGGTGTAGGTCA | 5187-5163 |
| 02-O-372 | (SEQ ID NO: 6) TACAACCTCAAGTGGTTCCTCTTCCCGA | 7017-7044 |
| 02-O-373 | (SEQ ID NO: 7) GAGGTCTGGATCTGCATGATGCGGA | 7897-7873 |
| 02-O-447 | (SEQ ID NO: 8) AACCCTTAGTATGTATTTGTATT | 9623-9645 |
| 02-O-476 | (SEQ ID NO: 9) CTCCTTCAACGTTGCGGTTCTGTCAG | 2739-2714 |
| 03-O-506 | (SEQ ID NO: 10) TTTTGCAAAGCGAACGATTCAGATG | 2427-2451 |
| 03-O-514 | (SEQ ID NO: 11) GCGGGACAAGCCGTTTTACGTTT | 2687-2709 |
| 03-O-542 | (SEQ ID NO: 12) GACGGGTGATTTATTTGATCTGCAC | 10766-10742 |
| 03-O-543 | (SEQ ID NO: 13) CATCTGAATCGTTCGCTTTGCAAAA | 2451-2427 |
| 03-O-564 | (SEQ ID NO: 14) CTACGTTCCAATGGAGCTCGACTGTC | 2324-2299 |
| 03-O-569 | (SEQ ID NO: 15) GGTCAAGTGGACACTTGGTCACTCA | 10150-10174 |
| 03-O-570 | (SEQ ID NO: 16) GAGTGAAGAGATAAGCAAGTCAAAG | 10275-10299 |
| 03-O-577 | (SEQ ID NO: 17) CATGTATACGTAAGTTTGGTGCTGG | 10376-10352 |
| 03-O-784 | (SEQ ID NO: 18) AATCCACAAGATTGGAGCAAACGAC | 2189-2213 |
| 67609 | (SEQ ID NO: 36) CGTATTACAATCGTACGCAATTCAG | 9862-9886 |
| 69240 | (SEQ ID NO: 37) GGATAAACAAACGGGACCATAGAAG | 9941-9965 |

[1]Location in sequence of Event DAS-59122-7 (see FIG. 1). Bases 1-2593 = 5' border, bases 2594-9936 = T-DNA insert, bases 9937-11922 = 3' border.

For verification of the DNA sequence that inserted into the maize genome, PCR was performed to amplify, clone, and sequence the inserted T-DNA from event DAS-59122-7. PCR primer sets, (SEQ ID NO: 11/SEQ ID NO:5); (SEQ ID NO: 4/SEQ ID NO:7); and (SEQ ID NO: 6/SEQ ID NO:3) shown in Table 3 were used to amplify three overlapping fragments labeled 22I-1 (SEQ ID NO: 25), 22I-2 (SEQ ID NO: 26), and 22I-3 (SEQ ID NO: 27) representing sequence from the 5' region of the T-DNA running through to the 3' region of the T-DNA insert from bp 2687 to bp 9846 for event DAS-59122-7 (see FIG. 1). PCR amplicon information is reported in Table 3 and primer sequences are listed in Table 2.

TABLE 3

PCR Primer and Amplicon Descriptions

| PCR Amplicon | Size (bp) | Target Sequence | Forward Primer | Reverse Primer | Location of PCR Amplicon (bp to bp)[1] |
|---|---|---|---|---|---|
| 22I-1 (SEQ ID NO: 25) | 2501 | T-DNA insert | 03-O-514 (SEQ ID NO: 11) | 02-O-371 (SEQ ID NO: 5) | 2687-5187 |
| 22I-2 (SEQ ID NO: 26) | 3027 | T-DNA insert | 02-O-370 (SEQ ID NO: 4) | 02-O-373 (SEQ ID NO: 7) | 4871-7897 |
| 22I-3 (SEQ ID NO: 27) | 2830 | T-DNA insert | 02-O-372 (SEQ ID NO: 6) | 02-O-227 (SEQ ID NO: 3) | 7017-9846 |
| O784/O564 (SEQ ID NO: 28) | 136 | 5' genomic border | 03-O-784 (SEQ ID NO: 18) | 03-O-564 (SEQ ID NO: 14) | 2189-2324 |
| O784/O543 (SEQ ID NO: 29) | 263 | 5' genomic border | 03-O-784 (SEQ ID NO: 18) | 03-O-543 (SEQ ID NO: 13) | 2189-2451 |
| O569/O577 (SEQ ID NO: 30) | 227 | 3' genomic border | 03-O-569 (SEQ ID NO: 15) | 03-O-577 (SEQ ID NO: 17) | 10150-10376 |
| O570/O542 (SEQ ID NO: 31) | 492 | 3' genomic border | 03-O-570 (SEQ ID NO: 16) | 03-O-542 (SEQ ID NO: 12) | 10275-10766 |
| O784/O215 (SEQ ID NO: 32) | 555 | 5' junction | 03-O-784 (SEQ ID NO: 18) | 02-O-215 (SEQ ID NO: 1) | 2189-2743 |
| O219/O577 (SEQ ID NO: 33) | 547 | 3' junction | 02-O-219 (SEQ ID NO: 2) | 03-O-577 (SEQ ID NO: 17) | 9830-10376 |
| O506/O476 | 313 | 5' junction | 03-O-506 | 02-O-476 | 2427-2739 |

TABLE 3-continued

PCR Primer and Amplicon Descriptions

| PCR Amplicon | Size (bp) | Target Sequence | Forward Primer | Reverse Primer | Location of PCR Amplicon (bp to bp)[1] |
|---|---|---|---|---|---|
| (SEQ ID NO: 34) O447/O577 (SEQ ID NO: 35) | 754 | 3' junction | (SEQ ID NO: 10) 02-O-447 (SEQ ID NO: 8) | (SEQ ID NO: 9) 03-O-577 (SEQ ID NO: 17) | 9623-10376 |
| 67609/69240 (SEQ ID NO: 38) | 104 | 3' junction | 67609 (SEQ ID NO: 36) | 69240 (SEQ ID NO: 37) | 9862-9965 |

[1]Location in sequence of Event DAS-59122-7 (see FIG. 1). Bases 1-2593 = 5' border, bases 2594-9936 = T-DNA insert, bases 9937-11922 = 3' border.

PCR GC2 Advantage™ Polymerase kit (BD Biosciences Clontech, Inc.) was used according to manufacturer's instructions to amplify the insert fragments (22I-1 (SEQ ID NO: 25), 22I-2 (SEQ ID NO: 26), and 22I-3 (SEQ ID NO: 27)). Briefly, a 50 µL reaction contained 5' and 3' primers at a final concentration of 0.2 µM and 40 ng of genomic DNA. PCR reactions were set up in duplicate using genomic DNA preparation from plants DAS-59122-7 T1S2 1 and DAS-59122-7 T1S2 2. PCR conditions were as follows: initial denaturation at 95° C. for 1 min, followed by 35 cycles of 94°/95° C. for 30 sec, 55° C. for 30 sec, and 68° C. for 5 min, with final extension at 68° C. for 6 min. PCR amplification products were visualized under UV light, following electrophoresis through a 1% agarose gel in 1×TBE (89 mM Tris-Borate, 2 mM EDTA, pH 8.3) stained with ethidium bromide.

PCR fragments 22I-1 (SEQ ID NO: 25), 22I-2 (SEQ ID NO: 26), and 22I-3 (SEQ ID NO: 27) were purified by excising the fragments from 0.8% agarose gel in 1×TBE stained with ethidium bromide, and purifying the fragment from the agarose using a QIAquick Gel Extraction Kit (Qiagen). PCR fragments were cloned into a pGEM-T Easy plasmid vector using the pGEM-T Easy Vector System I (Promega Corp.). Cloned fragments were verified by minipreparation of the plasmid DNA (QIAprep Spin Miniprep Kit, Qiagen) and restriction digestion with Not I. Plasmid clones and/or purified PCR insert fragments were then sent for sequencing of the complete insert. Sequencing reactions were carried with primers designed to be specific for known T-DNA sequences or with primers specific for use with the pGEM-T Easy vector. Sigma-Genosys, Inc. (The Woodlands, Tex.) synthesized all PCR primers, which were used at a final concentration of 0.2-0.4 µM in the PCR reactions.

PCR reactions with genomic DNA isolated from B.t. Cry34/35Ab1 events DAS-59122-7, DAS-45214-4, and DAS-45216-6, and unmodified control lines Hi-II and PH09B were used to confirm (1) the presence of maize genomic DNA in the sequenced border regions of event DAS-59122-7, and (2) event specific amplification across the junctions of the T-DNA insert and genomic DNA borders in event DAS-59122-7.

PCR primers designed to amplify the border sequence flanking the insert in event DAS-59122-7 were used to confirm the presence of those regions in unmodified control lines as well as in event DAS-59122-7. Two (2) sets of primers each, for the 5' and 3' borders (four (4) sets total) were tested. Primer sets 03-O-784/03-O-564 (SEQ ID NO: 18/SEQ ID NO:14) and 03-O-784/03-O-543 (SEQ ID NO: 18/SEQ ID NO:13) were used to amplify 136 bp and 263 bp fragments, respectively, from border sequence 5' to the T-DNA insert in event DAS-59122-7 (FIGS. 2 and 3). Similarly, primer sets 03-O-569/03-O-577 (SEQ ID NO: 15/SEQ ID NO:17) and 03-O-570/03-O-542 (SEQ ID NO: 16/SEQ ID NO:12) were used to amplify 227 bp and 492 bp fragments, respectively, from the 3' genomic border (FIGS. 2 and 3).

Primers designed to amplify fragments across the junction of the border sequence and T-DNA insert were used to establish event-specific PCR fragments for event DAS-59122-7. One primer set was selected for each of the two junctions. Primer set 03-O-784/02-O-215 (SEQ ID NO: 18/SEQ ID NO:1) was designed to amplify a 555 bp fragment across the 5' junction, and primer set 02-O-219/03-O-577 (SEQ ID NO: 2/SEQ ID NO:17) was designed for amplification of a 547 bp fragment at the 3' junction. A set of primers, IVR1(O197) (SEQ ID NO: 39) 5'-CCGCTGTATCACAAGGGCTGG-TACC-3' and IVR2(O198) (SEQ ID NO: 40) 5'-GGAGC-CCGTGTAGAGCATGACGATC-3', based on the endogenous maize invertase gene (Hurst et al., (1999) *Molecular Breeding* 5 (6):579-586), was used to generate a 226 bp amplification product as an internal positive control for all maize genomic DNA samples.

All PCR primers were synthesized by Sigma-Genosys, Inc. and used at a final concentration of 0.2-0.4 µM in the PCR reactions. PCR primer sequences are listed in the Table 2. For PCR amplifications, Advantage™-GC 2 PCR kit (BD Biosciences) was used according to manufacturer's instructions. Approximately 10-100 ng of genomic DNA template was used per 50 µL PCR reaction. PCR conditions were as follows: initial template denaturation at 94° C. for 5 min, followed by 35 cycles of 95° C. for 1 minute, 60° C. for 2 minutes, and 72° C. for 3 min, with final extension at 72° C. for 7 min. The PCR amplification products were visualized under UV light following electrophoresis through a 1% agarose gel with 1× TBE and ethidium bromide.

Sequence data obtained for the T-DNA insert and border regions of event DAS-59122-7 was reviewed and assembled using Seqman II™ software Version 4.0.5 (DNAStar, Inc., Madison, Wis.). The 5' and 3' border sequences flanking the insert present in event DAS-59122-7 were used for homology searching against the GenBank public databases in order to further characterize the site of insertion in the maize genome. Analysis to identify open reading frames in the junction regions between the flanking borders and T-DNA insert in event DAS-59122-7 was conducted using Vector NTI 8.0 (InforMax™, Inc., Frederick, Md.).

In total, 11922 bp of sequence from genomic DNA of event DAS-59122-7 was confirmed (see FIG. 1). At the 5' end of the T-DNA insert, 2593 bp of flanking border sequence was identified, and 1986 bp of flanking border sequence was obtained on the 3' end from fragments derived from genome walking experiments. A total of 7160 bp of the T-DNA insert was cloned and sequenced using PCR primer sets designed to amplify three overlapping fragments labeled 22I-1 (2501 bp) (SEQ ID NO:25), 22I-2 (3027 bp) (SEQ ID NO:26), and 22I-3 (2830 bp) (SEQ ID NO:27) representing sequence from the 5' region of the T-DNA running through to the 3' region of the T-DNA insert for event DAS-59122-7 from bp 2687 to bp 9846 (see FIG. 1). The remainder of the T-DNA insert region was sequenced from two PCR fragments, O506/O476 (SEQ ID NO: 10/SEQ ID NO:9) and O447/577 (SEQ ID NO: 8/SEQ ID NO:17) that spanned the 5' and 3' junctions, respectively, of the T-DNA insert with corn genomic DNA. Primers used were designed based on the sequence obtained from the genome walking experiments to amplify a fragment spanning the unique junction of the T-DNA with the corn genomic DNA. Primer set 03-O-506/03-O-476 (SEQ ID NO: 10/SEQ ID NO:9) spanned the 5' junction and amplified a 313 bp fragment (from bp 2427 to bp 2739) and primer set 03-O-447/03-O-577 (SEQ ID NO: 8/SEQ ID NO:17) spanned the 3' junction and amplified a 754 bp fragment (from bp 9623 to bp 10376). Combined, a total of 7343 bp of the T-DNA insert in event DAS-59122-7 was cloned and sequenced (from bp 2594 to bp 9936, see FIG. 1) and compared to the sequence of the transforming plasmid, PHP17662. Two nucleotide differences at bp 6526 and bp 6562 were observed in the non-translated wheat peroxidase promoter region of the T-DNA insert (see FIG. 1). Neither of the observed base changes affected the open reading frame composition of the T-DNA insert. Both the 3' and 5' end regions of the T-DNA insert were found to be intact, except for deletion of the last 22 bp at the 5' end and 25 bp at the 3' end encompassing the Right and Left T-DNA Border regions, respectively. While T-DNA border sequences are known to play a critical role in T-DNA insertion into the genome, this result is not unexpected since insertions are often imperfect, particularly at the Left T-DNA Border (Tinland (1996) *Trends in Plant Science* 1(6):178-184).

BLAST (Basic Local Alignment Search Tool) analysis of the genomic border regions of event DAS-59122-7 showed limited homology with publicly available sequences (Release 138.0 GenBank, Oct. 25, 2003). Analysis of the 5' border region found two areas with significant homology to maize genomic and EST (Expressed Sequence Tag) sequences. The first area encompasses 179 bp (bp 477 to bp 655 of the border sequence) and displays similarity to several molecular markers, chromosomal sequences, and consensus sequences obtained by alignment of various ESTs. The second area occurs at bp 1080 to bp 1153 (74 bp) of the 5' border sequence, and shows similarity to a number of different maize ESTs and genomic sequences. The 3' border region also had two small non-contiguous regions of similarity to plant DNA sequences. The inner 3' region of 162 bp (bp 9954 to bp 10115) showed similarity to the 3' untranslated end of two genomic *Zea mays* alcohol dehydrogenase (adh1) genes as well as to several EST consensus sequences. A smaller region (57 bp) in the middle of the 3' border (bp 10593 to bp 10649) showed similarity to non-coding regions from multiple maize genomic sequences.

Overall, no homologous regions greater than 179 base pairs were identified in either of the genomic border sequences, nor was more than one homologous region from the same known sequence found. Individual accessions displaying similarity to the event DAS-59122-7 border sequences were examined to determine if the insertion in event DAS-59122-7 occurred in a characterized protein coding sequence. None of the regions of similarity occurred within any known protein coding sequences. Local alignment of the entire transformation plasmid sequence, PHP17662, with the event DAS-59122-7 border sequences showed no significant homologies, indicating that the border regions flanking the T-DNA insert did not contain fragments of the transforming plasmid. Therefore, identification and characterization of the genomic sequence flanking the insertion site in event DAS-59122-7 was limited due to the absence of significant regions of homology to known sequences.

The 5' and 3' junction regions between the maize genomic border sequence and the T-DNA insert in event DAS-59122-7 were analyzed for the presence of novel open reading frames. No open reading frames of significant size (>100 amino acids) were identified in the 5' or 3' border junction regions, indicating that no novel open reading frames were generated as a result of the T-DNA insertion. Additionally, the homology searches did not indicate the presence of endogenous maize open reading frames in the border regions that might have been interrupted by the T-DNA insertion in B.t. Cry34/35Ab1 event DAS-59122-7.

Example 5

PCR Primers

DNA event specific primer pairs were used to produce an amplicon diagnostic for DAS-59122-7. These event primer pairs include, but are not limited to, SEQ ID NO: 18 and SEQ ID NO: 1; SEQ ID NO: 2 and SEQ ID NO: 17; SEQ ID NO: 10 and SEQ ID NO: 9; and SEQ ID NO: 8 and SEQ ID NO: 17; and SEQ ID NO: 36 and SEQ ID NO: 37. In addition to these primer pairs, any primer pair derived from SEQ ID NO: 21 and SEQ ID NO: 22 that when used in a DNA amplification reaction produces a DNA amplicon diagnostic for DAS-59122-7 is an embodiment of the present invention. Any modification of these methods that use DNA primers or complements thereof to produce an amplicon DNA molecule diagnostic for DAS-59122-7 is within the ordinary skill of the art. In addition, control primer pairs, which include IVR1 (O197)/IVR2(O198) (SEQ ID NO: 39/SEQ ID NO: 40) for amplification of an endogenous corn gene are included as internal standards for the reaction conditions.

The analysis of plant tissue DNA extracts to test for the presence of the DAS-59122-7 event should include a positive tissue DNA extract control (a DNA sample known to contain the transgenic sequences). A successful amplification of the positive control demonstrates that the PCR was run under conditions that allow for the amplification of target sequences. A negative, or wild-type, DNA extract control in which the template DNA provided is either genomic DNA prepared from a non-transgenic plant, or is a non-DAS-59122-7 transgenic plant, should also be included. Additionally a negative control that contains no template corn DNA extract will be a useful gauge of the reagents and conditions used in the PCR protocol.

Additional DNA primer molecules of sufficient length can be selected from SEQ ID NO: 21 and SEQ ID NO: 22 by those skilled in the art of DNA amplification methods, and conditions optimized for the production of an amplicon diagnostic for event DAS-59122-7. The use of these DNA primer sequences with modifications to the methods shown in these Examples are within the scope of the invention. The amplicon wherein at least one DNA primer molecule of sufficient length derived from SEQ ID NO: 21 and SEQ ID NO: 22 that is diagnostic for event DAS-59122-7 is an embodiment of the invention. The amplicon wherein at least one DNA primer of sufficient length derived from any of the genetic elements of PHI17662A that is diagnostic for event DAS-59122-7 is an embodiment of the invention. The assay for the DAS-59122-7 amplicon can be performed by using a Stratagene Robocycler, MJ Engine, Perkin-Elmer 9700, or Eppendorf Mastercycler Gradient thermocycler, or by methods and apparatus known to those skilled in the art.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. An isolated DNA molecule comprising a junction sequence comprising a sequence selected from the group consisting of SEQ ID NO: 33, 35, and complements thereof.

2. An insect resistant corn plant, or part thereof, comprising corn event DAS-59122-7, wherein DNA having at least one nucleotide sequence selected from the group consisting of SEQ ID NO: 33, 35, and complements thereof forms part of the plant's genome.

3. A descent plant of the insect resistant corn plant of claim 2, wherein DNA having at least one nucleotide sequence selected from the group consisting of SEQ ID NO: 33, 35, and complements thereof, forms part of the descent plant's genome, wherein said descent plant comprises corn event DAS-59122-7.

4. A seed of the plant of claim 2, wherein DNA having at least one nucleotide sequence selected from the group consisting of SEQ ID NO: 33, 35, and complements thereof, forms part of the seed's genome, wherein said seed comprises corn event DAS-59122-7.

5. A seed of the plant of claim 3, wherein DNA having at least one nucleotide sequence selected from the group consisting of SEQ ID NO: 33, 35, and complements thereof, forms part of the seed's genome, wherein said seed comprises corn event DAS-59122-7.

6. A method of producing an insect resistant corn plant, said method comprising breeding with the plant of claim 2, and selecting progeny by analyzing for at least one nucleotide sequence selected from the group consisting of SEQ ID NO: 33, 35, and complements thereof, wherein said progeny comprises corn event DAS-59122-7.

7. A method of producing an insect resistant corn plant, said method comprising breeding with the plant of claim 3, and selecting progeny by analyzing for at least one nucleotide sequence selected from the group consisting of SEQ ID NO: 33, 35, and complements thereof, wherein said progeny comprises corn event DAS-59122-7.

8. A method of detecting event DAS-59122-7 in corn tissue, said method comprising:
   (a) contacting a sample of said corn tissue with a polynucleotide probe that hybridizes under stringent hybridization conditions with one or more DNA sequences selected from the group consisting of SEQ ID NO: 33, 35, and complements thereof;
   (b) subjecting said sample and probe to stringent hybridization conditions; and
   (c) analyzing for hybridization of the probe.

* * * * *